US008563272B2

(12) United States Patent
Galvez, III et al.

(10) Patent No.: US 8,563,272 B2
(45) Date of Patent: Oct. 22, 2013

(54) CELLULOSIC PROTEIN EXPRESSION IN YEAST

(75) Inventors: Adriano Galvez, III, Visalia, CA (US); Glenn Richards, Visalia, CA (US)

(73) Assignee: Edeniq, Inc., Visalia, CA (US)

( * ) Notice: Subject to any disclaimer, the term of this patent is extended or adjusted under 35 U.S.C. 154(b) by 290 days.

(21) Appl. No.: 13/000,919

(22) PCT Filed: Jun. 26, 2009

(86) PCT No.: PCT/US2009/048872
§ 371 (c)(1),
(2), (4) Date: Mar. 29, 2011

(87) PCT Pub. No.: WO2009/158627
PCT Pub. Date: Dec. 30, 2009

(65) Prior Publication Data
US 2011/0177560 A1     Jul. 21, 2011

Related U.S. Application Data

(60) Provisional application No. 61/076,533, filed on Jun. 27, 2008.

(51) Int. Cl.
| C12P 19/00 | (2006.01) |
| C12N 1/19 | (2006.01) |
| C12N 9/24 | (2006.01) |
| C12N 9/42 | (2006.01) |
| C12N 9/44 | (2006.01) |
| C12N 9/02 | (2006.01) |

(52) U.S. Cl.
USPC .......... 435/72; 435/254.2; 435/200; 435/209; 435/210; 435/189

(58) Field of Classification Search
USPC ................ 435/72, 254.2, 200, 209, 210, 189
See application file for complete search history.

(56) References Cited

U.S. PATENT DOCUMENTS

| 5,633,146 A | 5/1997 | Fleer et al. |
| 5,830,463 A | 11/1998 | Duke et al. |
| 5,959,082 A | 9/1999 | Cosgrove et al. |
| 6,143,543 A | 11/2000 | Michelsen et al. |
| 6,218,167 B1 | 4/2001 | Allen et al. |
| 6,326,470 B1 | 12/2001 | Cosgrove |
| 6,365,390 B1 | 4/2002 | Blum et al. |

(Continued)

FOREIGN PATENT DOCUMENTS

| WO | WO 99/46363 | 9/1999 |
| WO | WO 2004/011025 | 2/2004 |

(Continued)

OTHER PUBLICATIONS

Result 1, from search of instant SEQ ID No. 5 in the Issued U.S. patents protein database, performed on Apr. 12, 2013.*

(Continued)

*Primary Examiner* — Rosanne Kosson
(74) *Attorney, Agent, or Firm* — Kilpatrick Townsend & Stockton LLP

(57) ABSTRACT

The present invention provides for combinations of enzymes and other proteins that result in improved saccharification of plant material. The invention provides for saccharification in the presence of and optional fermentation by, yeast cells expressing the enzymes and other proteins.

12 Claims, 2 Drawing Sheets

Alpha Expansin alignment

```
MAIAG--VLFLLF-----LARQASAAGYGGWQSAHATFYGGGDASGT
MAAAASALLLLLCSAFCSLAHRAAGVDYGSWQSAHATFYGGGDASGT
MK-MALAYGFCLVGLLAMVS-CAHAYGGGGWVNARATFYGGGDASGT
MRSMELVKSIALASLLTFIWLLTGAHGYGGWESAHATFYGGSDASGT
MXXXXXXXXXLXXXXXXXXXXXXXXXXGXWXXAXATFYGGXDASGT

MGGACGYGNLYSQGYGTNTAALSTALFNDGAACGSCYELRCDNAGSSCLPGSITVTAT
MGGACGYGNMYSTGYGTNTAALSTALFNDGAACGSCYELRCDNNGQSCLPGTITVTAT
MGGACGYGNLYSQGYGTNTAALSTALFNNGLGCGSCYEIRCVSDPKWCLPGAIVVTAT
MGGACGYGNLYSQGYGTNTAALSTALFNDGLSCGACYEMRCNDDPQWCLPGTVTVTAT
MGGACGYGNXYSXGYGTNTAALSTALFNXGXXCGXCYEXRCXXXXXXCLPGXXXVTAT

NFCPPNYGLPSDDGGWCNPPRPHFDMAEPAFLHIAQYRAGIVPVSFRRVPCVKKGGIR
NFCPPNYGLPSDDGGWCNPPRPHFDMAQPAFLQIAQYRAGIVPVAYRRVPCVKKGGIR
NFCPPNNALPNNAGGWCNPPQHHFDLSQPVFQHIAQYKAGVVPVAYRRVPCRRRGGIR
NFCPPNNALPNDNGGWCNPPLQHFDMAEPAFLKIAKYRGGIVPILYTRVPCLRKGGIR
NFCPPNXXLPXXXGGWCNPPXXHFDXXXPXFXXIAXYXXGXVPXXXXRVPCXXXGGIR

FTVNGHSYFNLVLVTNVAGAGDVRSVSIKGSRTGWQPMSRNWGQNWQSNAFLDGQS
FTINGHSYFNLVLVTNVAGAGDVQSVSIKGSSTGWQPMSRNWGQNWQSNSLLDGQS
FTINGHSYFNLVLITNVGGAGDVHSVSVKGSRTGWQAMSRNWGQNWQSNSYLNGQS
FTVNGHSYFNLVLITNVGGAGDVHAVSIKGSRSGWQPMSRNWGQNWQSNSYLNGQS
FTXNGHSYFNLVLXTNVXGAGDVXXVSXKGSXXGWQXMSRNWGQNWQSNXXLXGQS

LSFQVTASDGRTVTSNNVAHPGWQFGQTFEGGQF-
LSFQVTASDGRTVTSNGVAPAGWQFGQTFEGAQF-
LSFKVTTSDGRTVVSYNAAPAGWSFGQTYSGAQFR
LSFQVTTSDGRTVVSNNVAPSNWQFGQTFEGSQV-
LSFXVTXSDGRTVXSXXXAXXXWXFGQTXXGXQXX
```

(56) References Cited

U.S. PATENT DOCUMENTS

| | | | |
|---|---|---|---|
| 6,368,833 | B1 | 4/2002 | Borneman et al. |
| 6,682,738 | B1 | 1/2004 | Cosgrove |
| 6,828,136 | B2 | 12/2004 | Borneman et al. |
| 6,967,246 | B2 | 11/2005 | Swanson et al. |
| 7,226,756 | B2 | 6/2007 | Cosgrove et al. |
| 2003/0104546 | A1 | 6/2003 | Swanson et al. |
| 2003/0221224 | A1 | 11/2003 | Zinselmeier et al. |
| 2004/0115790 | A1 | 6/2004 | Pakula et al. |
| 2005/0233458 | A1 | 10/2005 | Cosgrove et al. |
| 2005/0272041 | A1 | 12/2005 | Cosgrove et al. |

FOREIGN PATENT DOCUMENTS

| | | |
|---|---|---|
| WO | WO 2007/084711 | 7/2007 |
| WO | WO 2007/115723 | 10/2007 |
| WO | WO 2008/021379 | 2/2008 |
| WO | WO 2008/064314 | 5/2008 |

OTHER PUBLICATIONS

International Preliminary Examination Report and Written Opinion dated Jan. 5, 2011, issued in related International Patent Application No. PCT/US2009/048872, filed Jun. 26, 2009.

Bayer et al., "The Potential of Cellulaseas and Cellulosomes for Cellulosis waste management," 2007, Curr. Opinion in Biotechnology, 18, 237-245.

Murai et al., "Assimilation of Cello-oligosaccharides by a Cell-Engineered Yeast Expressing Beta-Glucosidase and Carboxymethylcellulase From *Aspergillus aculeatus*," 1998, Applied and Environmental Microbiology, vol. 64, No. 12, pp. 4857-4861.

Ueda et al., "Genetic Immobilization of Proteins on the Yeast Cell Surface," 2000, Biotechnology Advances, vol. 18, Issue 2, pp. 121-140.

Van Rensburg et al., "Engineering Yeast for Efficient Cellulose Degradation," 1998, Yeast, 14(1); pp. 67-76.

International Search Report dated Dec. 10, 2009, issued in related International Patent Application No. PCT/US2009/048872, filed Jun. 26, 2009.

Kim et al., "Functional Characterization of a Bacterial Expansin from *Bacillus subtilis* for Enhanced Enzymatic Hydrosis of Cellulose," 2009, Biotechnology and Bioengineering, vol. 102, No. 5, 1342-1353.

Micolonghi et al., "Heterologous products from the Yeast Kluyveromyces latis: exploration of KlPDC1, a single-gene based system," Communicating Current Research and Educational Topics and Trends in Applied Microbiology [Online], 2007, vol. 1, pp. 271-282, Retrieved from the internate: <URL: http://www.formatex.org/microbio/pdf/Pages271-282.pdf>.

* cited by examiner

Figure 1
Alpha Expansin alignment

```
MAIAG--VLFLLF-----LARQASAAGYGGWQSAHATFYGGGDASGT
MAAAASALLLLLCSAFCSLAHRAAGVDYGSWQSAHATFYGGGDASGT
MK-MALAYGFCLVGLLAMVS-CAHAYGGGGWVNARATFYGGGDASGT
MRSMELVKSIALASLLTFIWLLTGAHGYGGWESAHATFYGGSDASGT
MXXXXXXXXXXLXXXXXXXXXXXXXXXXGXWXXAXATFYGGXDASGT

MGGACGYGNLYSQGYGTNTAALSTALFNDGAACGSCYELRCDNAGSSCLPGSITVTAT
MGGACGYGNMYSTGYGTNTAALSTALFNDGAACGSCYELRCDNNGQSCLPGTITVTAT
MGGACGYGNLYSQGYGTNTAALSTALFNNGLGCGSCYEIRCVSDPKWCLPGAIVVTAT
MGGACGYGNLYSQGYGTNTAALSTALFNDGLSCGACYEMRCNDDPQWCLPGTVTVTAT
MGGACGYGNXYSXGYGTNTAALSTALFNXGXXCGXCYEXRCXXXXXXCLPGXXXVTAT

NFCPPNYGLPSDDGGWCNPPRPHFDMAEPAFLHIAQYRAGIVPVSFRRVPCVKKGGIR
NFCPPNYGLPSDDGGWCNPPRPHFDMAQPAFLQIAQYRAGIVPVAYRRVPCVKKGGIR
NFCPPNNALPNNAGGWCNPPQHHFDLSQPVFQHIAQYKAGVVPVAYRRVPCRRRGGIR
NFCPPNNALPNDNGGWCNPPLQHFDMAEPAFLKIAKYRGGIVPILYTRVPCLRKGGIR
NFCPPNXXLPXXXGGWCNPPXXHFDXXXPXFXXIAXYXXGXVPXXXXRVPCXXXGGIR

FTVNGHSYFNLVLVTNVAGAGDVRSVSIKGSRTGWQPMSRNWGQNWQSNAFLDGQS
FTINGHSYFNLVLVTNVAGAGDVQSVSIKGSSTGWQPMSRNWGQNWQSNSLLDGQS
FTINGHSYFNLVLITNVGGAGDVHSVSVKGSRTGWQAMSRNWGQNWQSNSYLNGQS
FTVNGHSYFNLVLITNVGGAGDVHAVSIKGSRSGWQPMSRNWGQNWQSNSYLNGQS
FTXNGHSYFNLVLXTNVXGAGDVXXVSXKGSXXGWQXMSRNWGQNWQSNXXLXGQS

LSFQVTASDGRTVTSNNVAHPGWQFGQTFEGGQF-
LSFQVTASDGRTVTSNGVAPAGWQFGQTFEGAQF-
LSFKVTTSDGRTVVSYNAAPAGWSFGQTYSGAQFR
LSFQVTTSDGRTVVSNNVAPSNWQFGQTFEGSQV-
LSFXVTXSDGRTVXSXXXAXXXWXFGQTXXGXQXX
```

Figure 2
Beta Expansin alignment

```
MGSVS--YVLAAAVLAALVSGGACIP-KVPPGPNITTNYNNQWLSAKATWYGRPTGSGPK
MASSK--MMLAMAVLAALLSLAHGIP-KVPPGPNITATYNGKWLDAKSTWYGRPEGAGPK
MGSLTTNIVLAVAVVAALVGGGSCGPPKVPPGPNITTNYNAPWLPARATWYGQPYGSGST
MGSLANNIMVVGAVLAALVVGGSCGPPKVPPGPNITTNYNGKWLTARATWYGQPNGAGAP
MXSXXXXXXXXXAVXAALXXXXXXXPXKVPPGPNITXXYNXXWLXAXXTWYGXPXGXGXX

DNGGACGIKDVNLAPYNGMIACGNVPIFKDGKGCGSCYEIKCQKPSP-CSDKPITIFITD
DNGGACGYKDVDKPPFNGMTSCGNTPIFRDGRGCGSCFEVKCEKPAEFCSGQPVLVHITD
DNGGACGIKNVNLPPYNGMISCGNVPIFKDGRGCGSCYEVKCEQPAA-CSKQPVTVFITD
DNGGACGIKNVNLPPYSGMTACGNVPIFKDGKGCGSCYEVRCKEKPE-CSGNPVTVFITD
DNGGACGXKXVXXXPXXGMXXCGNXPIFXDGXGCGSCXEXXCXXXXXXCSXXPXXXXITD

KNYEPIAPYHIDLSGTAFGAMATPGKEQTLRSFGELELQFRRVRCKYAPGTKITFHVEKG
DNEEPIAAYHFDLSGKAFGSMAKKGQEQKLRGCGEVEIQFRRVKCYYPLGTKVTYHVEKG
MNYEPISAYHFDFSGKAFGAMACPGKETELRKAGIIDMQFRRVRCKYPGGQKVTFHVEKG
MNYEPIAPYHFDLSGKAFGSLAKPGLNDKLRHCGIMDVEFRRVRCKYPAGQKIVFHIEKG
XNXEPIXXYHXDXSGXAFGXXAXXGXXXXLRXXGXXXXXFRRVXCXYXXGXKXXXHXEKG

SNPNYLAVLVKFVSDDGDVVQMDIQESKSPAWIPLTLSWGAIWRWDGAKPLKGPFSIRVT
SNPNYLALLVKFVGGDGDVVAVEVQEKGKYNWIPLKESWGAVWRIDTAKPLKGPLSVRYT
SNPNYLAVLVKFVADDGDVIQMDLQEAGLPAWRPMKLSWGAIWRMDTATPLKAPFSIRVT
CNPNYVAVLVKFVADDGDIVLMEIQDKLSAEWKPMKLSWGAIWRMDTAKALKGPFSIRLT
XNPNYXAXLVKFVXXDGDXXXXXXQXXXXXXWXPXXXSWGAXWRXDXAXXLKXPXSRXT

SESGKKLIAKDVIPANWKADTVYTSNVQF-
TDGGTKAVSPDVIPEKWKPDTMYVAKY---
TESGKSLIAKDVIPVNWMPDAIYVSNVQFY
SESGKKVIAKDIIPANWRPDAVYTSNVQFY
XXXGXXXXXXDXIPXXWXXDXXYXXXXXXX
```

CELLULOSIC PROTEIN EXPRESSION IN YEAST

CROSS-REFERENCE TO RELATED PATENT APPLICATIONS

The present application is the U.S. National Stage entry of International Application No. PCT/US2009/048872, filed Jun. 26, 2009, which claims benefit of priority to US Provisional Patent Application No. 61/076,533, filed Jun. 27, 2008, which is incorporated by reference for all purposes.

BACKGROUND OF THE INVENTION

REFERENCE TO A "SEQUENCE LISTING," A TABLE, OR A COMPUTER PROGRAM LISTING APPENDIX SUBMITTED AS AN ASCII TEXT FILE

The Sequence Listing written in file -1-1.TXT, created on May 3, 2013, 32,768 bytes, machine format IBM-PC, MS-Windows operating system, is hereby incorporated by reference in its entirety for all purposes.

Traditionally, enzymes used for saccharification or biofuels applications have been manufactured using fungal organisms including *Trichoderma* and *Aspergillus*. There are a number of species and many variants and mutants that have been made from these organisms over decades of research efforts targeted at increased activity. However, commercial enzymes are usually sold as monotonic liquids, meaning they contain mainly a single enzyme or are from a single organism.

BRIEF SUMMARY OF THE INVENTION

The present invention provides for isolated yeast cells that express at least two heterologous proteins, wherein the heterologous proteins are:
(a) an expansin, or an "expansin-like" protein; and
(b) a cellulase, a xylanase, an endoglucanase, a glucosidase, a glucanase, a ligninase and a cellobiase,
wherein the cell expresses at least one protein from group (a) and at least one protein from group (b).

In some embodiments, the expansin-like protein comprises SEQ ID NO:5 or SEQ ID NO:10. In some embodiments, the protein from group (a) is an expansin. In some embodiments, the yeast cell expresses both an alpha expansin and a beta expansin.

In some embodiments, the protein from group (a) is an expansin-like protein.

In some embodiments, the expansin-like protein is a swollenin.

In some embodiments, the proteins are secreted outside the yeast cell. In some embodiments, the proteins are linked to the yeast cell wall or cell membrane. In further embodiments, the proteins are expressed and retained in the cytoplasm.

In some embodiments, the yeast is selected from the group consisting of *Saccharomyces* ssp., *Schizosaccharomyces* ssp., *Candida* ssp., *Cryptococcus* ssp., *Hansenula* ssp., *Kluyveromyces* ssp. and *Pichia* ssp.

In some embodiments, the cell expresses:
(a) an expansin or a swollenin;
(b) a cellulase or a glucosidase; and
(c) a ligninase or a laccase.

In some embodiments, the cell expresses:
(a) an expansin or a swollenin;
(b) a cellulase and a glucosidase; and
(c) a ligninase or a laccase.

In some embodiments, the cell expresses:
(a) an expansin-like protein (including but not limited to a protein comprising SEQ ID NO:5 or SEQ ID NO:10. and/ or SEQ ID NO:11);
(b) a cellulose or a glucosidase; and
(c) a ligninase or a laccase.

The present invention also provides for isolated yeast cells that express at least three heterologous proteins, wherein the heterologous proteins are:
(a) a cellulase;
(b) a xylanase; and
(c) a ligninase or a laccase,
wherein the cell expresses at least one protein from group (a) and at least one protein from group (b) and at least one protein from group (c).

The present invention also provides for cell cultures comprising the yeast cell as described herein, further comprising a source of cellulose In some embodiments, the concentration of yeast cells is at least $10^4$, $10^5$ or $10^6$ cfu/ml.

The present invention also provides for cell cultures comprising at least two different yeast strains, the strains comprising:
(a) a first yeast strain that expresses at least one heterologous protein selected from a group in Table 1;
(b) a second yeast strain that that expresses at least one heterologous protein selected from a group in Table 1;
wherein the protein expressed in the first yeast strain is from a different group than the protein expressed in the second yeast strain.

In some embodiments, the cultures further comprise a third yeast strain, wherein the third yeast strain expresses a protein from a group of Table 1 that is a different group from the proteins expressed by the first and second yeast strains.

In some embodiments, the first yeast strain further expresses at least two proteins, wherein each of the two proteins are from different groups in Table 1 and are different groups from the protein expressed in the second strain.

In some embodiments, the cell culture comprises yeast cells that in sum express at least one protein from each group of Table 1.

In some embodiments, the yeast is selected from the group consisting of *Saccharomyces* ssp., *Schizosaccharomyces* ssp., *Candida* ssp., *Cryptococcus* ssp., *Hansenula* ssp., *Kluyveromyces* ssp. and *Pichia* ssp.

In some embodiments, the cell cultures described herein further comprise a source of cellulose.

In some embodiments, the concentration of yeast cells is at least $10^4$, $10^5$ or $10^6$ cfu/ml.

The present invention also provides for methods of converting a source of cellulose into sugars. In some embodiments, the method comprises incubating a source of cellulose in an aqueous medium in the presence of a cell culture described above or elsewhere herein under conditions to allow the enzymes expressed from the yeast to convert cellulose in the source into sugar.

In some embodiments, the source of cellulose is at least 5% cellulose.

In some embodiments, the source of cellulose is selected from the group consisting of wood, distillers grain, sugar cane, rice straw, rice hulls, wheat straw, switchgrass, waste agricultural material, sawdust, recycled building materials, paper, cardboard, composite board, sludge, corn stover, whole corn, ground corn, corn silage, sorghum, and energy cane.

In some embodiments, the sugar formed by the method is fermented by the yeast to produce alcohols.

In some embodiments, the concentration of yeast cells is at least $10^4$, $10^5$ or $10^6$ cfu/ml.

BRIEF DESCRIPTION OF THE DRAWINGS

FIG. 1: Alpha expansin alignment (SEQ ID NOS:1-4), consensus =SEQ ID NO:12.

FIG. 2: Beta expansin alignment (SEQ ID NOS:6-9), consensus =SEQ ID NO:13.

DEFINITIONS

As used throughout the specification and in the appended claims, the singular forms "a," "an," and "the" include the plural reference unless the context clearly dictates otherwise.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

"Conservatively modified variants" applies to both amino acid and nucleic acid sequences. With respect to particular nucleic acid sequences, "conservatively modified variants" refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein that encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants of the proteins of the present invention are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins* (1984)).

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., at least 60% identity, optionally at least 65%, 70%, 75%, 80%, 85%, 90%, 95%, 98%, or 99% identity over a specified region (or the whole reference sequence when not specified)), when compared and aligned for maximum correspondence over a comparison window, or designated region as measured using one of the following sequence comparison algorithms or by manual alignment and visual inspection. For example, the present invention provides for polypeptides comprising an amino acid sequence substantially identical to any of SEQ ID NOs: 1, 2, 3, 4, 5, 6, 7, 8, 9, 10, or 11, or any sequences as set forth in Table 1. Sequences having less than 100% identity but that have at least one of the specified percentages are said to be "substantially identical." Optionally, the identity exists over a region that is at least about 50 nucleotides in length, or more preferably over a region that is 100 to 500 or 1000 or more nucleotides in length.

The term "similarity," or "percent similarity," in the context of two or more polypeptide sequences, refer to two or more sequences or subsequences that have a specified percentage of amino acid residues that are either the same or similar as defined in the 8 conservative amino acid substitutions defined above (i.e., 60%, optionally 65%, 70%, 75%, 80%, 85%, 90%, or 95% similar over a specified region), when compared and aligned for maximum correspondence over a comparison window, or designated region as measured using one of the following sequence comparison algorithms or by manual alignment and visual inspection. Sequences having less than 100% similarity but that have at least one of the specified percentages are said to be "substantially similar." Optionally, this identity exists over a region that is at least about 50 amino acids in length, or more preferably over a region that is at least about 100 to 500 or 1000 or more amino acids in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

Examples of an algorithm that is suitable for determining percent sequence identity and sequence similarity include the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

Cells that "in sum" express two or more proteins means that the cells, when taken together, express the two or more proteins. As an example, cells that in sum express proteins A and B can include a mixture of one strain of cells that express protein A only and a second strain of cells that expresses protein B only.

The term "recombinant" when used with reference, e.g., to a cell, or nucleic acid, protein, or vector, indicates that the cell, nucleic acid, protein or vector has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that otherwise are expressed abnormally, under-expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes or other nucleic acid sequences arranged to make a new functional nucleic acid, e.g., a promoter from one source and a coding region from another source.

An "expression cassette" is a nucleic acid construct, generated recombinantly or synthetically, with a series of specified nucleic acid elements that permit transcription of a particular nucleic acid in a host cell. The expression cassette can optionally be part of a plasmid, virus, or other nucleic acid fragment. Typically, the expression cassette includes a nucleic acid to be transcribed operably linked to a promoter.

The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

DETAILED DESCRIPTION

I. Introduction

The present invention provides for isolated yeast and yeast cultures useful for converting cellulose and other plant products into sugars (and optionally fermenting the sugars into alcohols). The inventors have discovered desirable combinations of proteins that result in surprisingly improved sugar production from cellulose sources. Further, expression of these protein combinations in yeast (as opposed to use of purified enzymes) removes the need for expensive and time-consuming protein purification steps. Further, the presence of yeast can also allow for fermentation of the sugars to alcohols. This achieves cellulose-to-alcohol production (saccharification and fermentation) in one reaction. In addition, the entire reaction efficiency can be improved as many cellulose degrading enzymes are inhibited by high levels of sugars. By simultaneously fermenting the sugars, the yeast allows for maintenance of high cellulose conversion rates.

II. Enzyme Combinations

The present invention provides for a variety of combinations of proteins wherein the combination of enzymes results in improved production of sugars from cellulose compared to single enzymes. Notably, the invention provides for combinations of three, four, five or more enzymes that results in greatly improved activities. While combinations of such a large number of purified enzymes is technically feasible, it is not generally commercially feasible due to cost of production of protein purification. Thus, in some embodiments of the invention, the combinations of enzymes are produced recombinantly from one or more microorganism strains to achieve a cell culture such that the combination of enzymes are expressed in the culture and are available to convert cellulose and/or other plant carbon sources. Five carbon sugars can be produced from hemicelluloses and the conversion of hemicellulose not only increases the amount of available sugar for use in production but it also disrupts the protective matrix protecting cellulose from enzymatic hydrolysis. While lignin does not break down into any sugars, lignases can assist in the overall conversion of cellulose and hemicelluloses by removing the lignin bond that helps protect cellulose and hemicelluloses from enzymatic hydrolysis.

As explained further herein, the combinations of proteins can be provided to a cellulose source by contacting the source with one or more microorganisms (e.g., yeast, bacteria, fungi) that in sum express the desired combination of proteins. Alternatively, multiple proteins can be expressed in a single microorganism strain. Thus, for example, where a combination of two proteins is desired, a single yeast strain can be engineered to recombinantly express both proteins, or two separate yeast strains, each producing one of the proteins, can be included. It will be recognized that as the number of proteins in the combinations increase, a variety of combinations of yeast strains can be employed to produce the same result. For example, where three proteins are to be combined, three separate strains, each expressing one protein, can be combined. Alternatively, one strain expressing all three proteins can be employed, or a combination of one strain expressing two proteins and a second strain expressing one protein can be employed. Thus, for any of the combinations described herein, it should be recognized that the expression of the combination of proteins can be achieved in different ways and each way is intended to be expressly disclosed.

Table 1 provides a list of proteins that can be used according to the invention, separated into different groups having different activities.

TABLE 1

| Group 1 | |
|---|---|
| Amylases | Glycoside hydrolase enzymes that convert starches into saccharides ranging from mono to polysaccharides. Examples include, but are not limited to: 1,4-α-D-glucan glucanohydrolase, 1,4-α-D-glucan maltohydrolase, 1,4-α glucosidase, amyloglucosidase, glucoamylase, as well as enzymes substantially similar to the amino acid sequences in Genbank accession numbers CAA00094, EAW10819, CAA00095, BAA01255, XP_755679, CAK40537, BAD06002, CAA31220, CAA3121. |
| Group 2 | |
| Cellulases | Enzymes that catalyze the cellulolysis of cellulose into smaller polysaccharide chains. Examples include, but are not limited to: cellobiase, endoglucanse, endo-1,4-beta-glucanase, carboxymethyl cellulose, beta-1,4-glucanase, beta-1,4-endoglucan hydrolase, as well as enzymes substantially similar to the amino acid sequences in Genbank accession numbers CAA43059, AAR29981, |

TABLE 1-continued

| | ABQ95572, AAQ21383, Q12714, BAA36216, ACC59774, P36218, and P48793. |
|---|---|
| Glucosidases | Glycoside hydrolases that catalyze the hydrolysis of glycosidic bonds into smaller sugars breaking cellulose and hemicellulose. Examples include, but are not limited to beta-glucosidase and enzymes substantially similar to the amino acid sequences in Genbank accession numbers AAF80600, AAQ21384, 1713235A, AAP57760, AAP57759, BAA74959, CAA93248, BAA74958, and XP_752815. |
| Group 3 | |
| Xylanases | Enzymes that break down hemicellulose or beta-1,4-xylan into xylose. These enzymes are also known as the "C5 sugar" enzymes and are found in many fungal organisms. Examples include, but are not limited to enzymes substantially similar to the amino acid sequences in Genbank accession numbers AAN78423, AAS37695, ACB38137, AAG01167, CAA49294, ABK59833, AAQ67413, AAP83925, and CAB60757. |
| Group 4 | |
| Expansins and Expansin-like proteins | These proteins are non-enzymatic proteins involved in cell growth and fruit softening. Examples include, but are not limited to, alpha-expansin (EXPA), beta-expansin (EXPB), as well as proteins substantially similar to the amino acid sequences in Genbank accession numbers CAA69105, AAB81662, AAB40639, AAB40636, AAB40635, AAL24494, AAL24489, AAM73781, and AAF72989. Expansin-like proteins are non-enzymatic proteins that act on fibrils and microfibrils from plants that are long strands of glucose monomers, thereby loosening the structure of the fibrils. Examples include, but are not limited to: expansin-like gene products, EXLA, EXLB, Swollenins, endoglucanases with cell wall extension activity as well as those described in U.S. Pat. No. 6,967,246 and proteins substantially similar to the amino acid sequences in Genbank accession numbers CAB92328, ACB05430, ABV57767, EDP47653, EAL85710, XP_747748, AAD47901, and AFUA_6G03280. |
| Group 5 | |
| Feruloyl Esterases | Enzymes that convert feruloyl-polysaccharides into ferulate and polysaccharides in the presence of water. Examples include, but are not limited to: ferulic acid esterase, hydroxycinnamoyl esterase, FAE-III, cinnamoyl ester hydrolase, FAE-A, cinnAE, FAE-I, FAE-II, as well as enzymes substantially similar to the amino acid sequences in Genbank accession numbers CAD44531, BAE44304, CAK45846, CAC85738, CAC05587, CAA70511, CAA70510, CAC14144, and AAF70241. |
| Lipases | Water soluble enzymes that catalyze the hydrolysis of ester bonds. Lipases are considered a subclass of esterases. Examples include, but are not limited to enzymes substantially similar to the amino acid sequences in Genbank accession |

TABLE 1-continued

| | |
|---|---|
| | numbers AAS55958, CAJ55827, AAP57750, AAO17921, ABV44404, ABS31353, ABM90643, AAB35245, and ABG73614. |
| Cutinases | Hydrolase enzymes acting on carboxylic ester bonds.<br>Examples include, but are not limited to:<br>cutin hydrolase,<br>serine esterase,<br>as well as enzymes substantially similar to the amino acid sequences in Genbank accession numbers CAB40372, AAA33334, CAA61622, ABR19840, CAA46582, AAB05922, AAX55266, AAM10822, and AAL67672. |
| Group 6 | |
| Ligninases | Lignin peroxidase enzymes.<br>Examples include, but are not limited to:<br>manganese peroxidase,<br>lignin peroxidase,<br>cellobiase dehydrogenase,<br>as well as enzymes substantially similar to the amino acid sequences in Genbank accession numbers AAA56852, CAA68373, S67522, AAA33733, P06181, BAG12560, ABQ44529, CAB51617, and CAA91043. |
| Laccases | Laccase is a oxidoreductase catalyst involved in coupling lignols.<br>Examples include, but are not limited to:<br>oxygen oxidoreductases,<br>extracellular copper-containing glycoproteins,<br>as well as enzymes substantially similar to the amino acid sequences in Genbank accession numbers AAA33592, AAA33591, CAA77015, AAB47734, AAQ12270, AAQ12269, AAQ12268, AAB47733, and CAA59161. |

Cellulases catalyze the cellulolysis of cellulose. Most celluloses identified to date are from fungi. Several different kinds of structurally-different cellulases are known. Moreover, mutations are known that can increase activity significantly. See, e.g., U.S. Pat. No. 7,364,891; Chand et al., *J. Applied Microbiol.* 98(2):318-323 (2005). Names used for various types of cellulases include: cellobiohydrolase I&II, endoglucanase I, II, III, & V; endo-1,4-beta-glucanase, carboxymethyl cellulase (CMC), beta-1,4-glucanase and beta-1,4-endoglucan hydrolase. There are several types of cellulases based on the type of reaction catalyzed: endo-cellulase breaks internal bonds to disrupt the crystalline structure of cellulose and expose individual cellulose polysaccharide chains. Exo-cellulase cleaves from the ends of the exposed chains produced by endocellulase, resulting in tetrasaccharides or disaccharides such as cellobiose. Cellobiase or beta-glucosidase hydrolyses the exo-cellulase into individual monosaccharides. Most fungal cellulases have a two-domain structure with one catalytic domain, and one cellulose binding domain. Some cellulases, mostly endoglucanases, lack a cellulose binding domain.

Expansins refer to a family of closely-related nonenzymatic proteins, found in plant cell walls, with roles in plant cell growth, fruit softening and developmental processes where cell wall loosening occurs. See, e.g., Sampedro et al., *Genome Biology* 6:242 (2005). A compilation of known expansin sequences is available on the world wide web at, for example, bio.psu.edu/expansins. Two families of expansin genes have been discovered in plants, named alpha-expansins and beta-expansins. At least one expansin crystal structure is available. See, e.g., Yennawar et al., *Proc. Natl. Acad. Sci. USA* 103:14664-14671 (2006). Expansins characteristically cause wall relaxation and irreversible wall creep. No enzymatic activity to date has been found for expansins. Relative expansin activity can be detected by measuring wall stress relaxation or wall extension. Expansin disrupts the adhesion of hemicellulose on the surface of cellulose microfibrils. Hemicellulose can tether cellulose microfibrils together, forming a strong load-bearing network.

Expansin-like proteins refer to expansin proteins as well as other non-enzymatic proteins that exhibit cellulose binding and cellulose weakening activities. Assays for testing a protein for cellulose binding and cellulose weakening activities are known in the art and art described in, e.g., Kim et al., *Biotechnology and Bioengineering* 102(5):1342-1353 (2009). Expansin-like proteins are known to have cell-wall loosening activity and are be involved in cell expansion and other developmental events during which cell-wall modification occurs. Proteins in this class of families binds tightly to the cell wall and stimulates cell-wall extension and stress relaxation. These proteins are not enzymatic in nature. Expansin like proteins often consist of two domains; domain 1 is homologous to the catalytic domain of proteins in the glycoside hydrolase family 45 (GH45); expansin domain 2 is homologous to group-2 grass pollen allergens, which are of unknown biological function. Experimental evidence suggests that expansins loosen cell walls via a nonenzymatic mechanism that induces slippage of cellulose microfibrils in the plant cell wall. Proteins capable of inducing slippage of the cellulose microfibrils are expansin-like in function. Expansin-like proteins are described in, e.g., Cosgrove, D J. (2000) Nature 407:321-326; Cosgrove D J, et al. (2002) *Plant Cell Physiol:* 43(12):1436-44; Darley C P et al. (2003) *FEBS Lett:* 10;546(2-3):416-8; and Yennawar et al. (2006) *Proc Natl Acad Sci USA.* 103(40):14664-71.

As noted above, the proteins EXLB and EXLA are exemplary expansin-like proteins. The structure of EXLB domain 1 resembles that of the family-45 glycoside hydrolase (GH45). However, EXLB lacks a second aspartate that serves as the catalytic base required for hydrolytic activity in GH45 enzymes. Domain 2 of EXLB is an Ig-like beta-sandwich, with aromatic and polar residues that form a potential surface for polysaccharide binding in line with the glycan binding cleft of domain 1. See, e.g., Yennawar et al. (2006) *Proc Natl Acad Sci USA.* 103(40):14664-71. EXLB binds to maize cell walls, most strongly to xylans, causing swelling of the cell wall.

A subset of alpha and beta expansin amino acid sequences are aligned in FIGS. 1 and 2, respectively, with the consensus sequence provided at the lowest line. In some embodiments of the invention, expansins comprise the amino acid sequences set forth in FIG. 1 or 2, or sequences substantially identical to those sequences. Notably, each of the figures provides a consensus sequence as their bottom sequence. SEQ ID NO:5 is based on the alpha expansin consensus. SEQ ID NOS:10 and 11 represent amino and carboxyl consensus portions for beta expansins. Thus, in some embodiments, expansin-like proteins comprise the amino acid sequence set forth in SEQ ID NO:5 or 10 and/or 11. Expansins and expansin-like proteins described in this and the above-paragraphs (including but not limited to proteins comprising SEQ ID NOS:1, 2, 3, 4, 5, 6, 7, 8, 9, 10, or 11) are intended to be considered part of Table 1.

Further, some expansin subsequences that show absolute identity within the alignments of FIGS. 1 and 2 include:
TWYG (SEQ ID NO:14) beta expansin motif (approximate amino acid position ~49-52)
GGACG (SEQ ID NO:15) alpha and beta expansin as well as swollenins (alpha approximate amino acid position ~62-67; beta approximate amino acid position ~63-67; swollenin approximate amino acid position ~190-200)

H(F/I)D alpha and beta expansin; where the second residue in the motif is either an F or an I (alpha approximate amino acid position ~143-145; beta approximate amino acid position 130-132)

ATFYGGXDASGTXXMGGACGYGNX-YSXGYGTNTAALSTALFN (SEQ ID NO:16) alpha expansin consensus (approximate amino acid position ~48-89)

VTATNFCPPNXXLPXXXGGWCNPP (SEQ ID NO:17) alpha expansin consensus (approximate amino acid position ~117-140)

IRFTXNGXXHSYFNLVLXTNVXGAGDVXXVSXKGS (SEQ ID NO:18) alpha expansin consensus (approximate amino acid position ~179-213)

MSRNWGQNWQSNXXLXGQXSLSFXVTXSDGRTV (SEQ ID NO:19) alpha expansin consensus (approximate amino acid position ~221-253)

KVPPGPNITXXYN (SEQ ID NO:20) beta expansin consensus (approximate amino acid position ~28-40)

CGNXPIFXDGXGCGSCXE (SEQ ID NO:21) beta expansin consensus (approximate amino acid position ~82-99)

ITDXNXEPIXXYHXDXSGXAFG (SEQ ID NO:22) beta expansin consensus (approximate amino acid position ~118-139)

EKGXNPNYXAXLVKFVXXDGD (SEQ ID NO:23) beta expansin consensus (approximate amino acid position ~178-198).

Accordingly, in some embodiments, the expansins of the invention comprise one or more of the above-listed subsequences.

Ligninases are enzymes that break down lignin. Lignin cross-links with the other cell wall components, which limits the accessibility of cellulose and hemicellulose to other enzymes. In some embodiments, ligninases employ free radicals for depolymerization reactions. Examples of such enzymes include, but are not limited to, manganese peroxidase, lignin peroxidase and cellobiose dehydrogenase. Lignin peroxidase (also ligninase) is a hemoprotein from the white-rot fungus with a variety of lignin-degrading reactions, dependent on hydrogen peroxide to incorporate oxygen into reaction products. Exemplary lignin peroxidases (LIP) are encoded, for example, from *Phanerochaete chrysosporium* or *Phlebia radiata*. For example, at least six heme proteins (H1, H2, H6, H7, H8, and H10) with LIP activity have been identified in *P. chrysosporium* strain BKMF-1767 of which isozymes H2, H6, H8, and H10 are the major LIPs in both static and agitated cultures of *P. chrysosporium*. See, e.g., U.S. Pat. No. 7,049,485. However, other fungi which produce ligninases suitable for use in the present invention include *Bjerkandera adusta, Trametes hirsuta, Plebia radiata, Pleurotus* spp., *Stropharia aurantiaca, Hypholoma fasciculare, Trametes versicolor, Gymnopilus penetrnas, Stereum hirsutum, Mycena haematopus,* and *Armillaria mellea* as well as those in Table 1. Other ligninases include, e.g., other enzymes that are involved in lignin biodegradation, such as manganese peroxidase, laccase and cellobiose dehydrogenase.

Xylanases are enzymes that degrade the linear polysaccharide beta-1,4-xylan into xylose. These enzymes therefore breakdown hemicellulose, which is a major component of the cell wall of plants. Xylanases are present in fungi for the degradation of plant matter.

It will be appreciated that either wildtype or synthetic enzymes can be expressed in yeast as described herein. Examples of synthetic enzymes include proteins having amino acid sequences derived from naturally occurring enzyme sequences that have been mutated to improve or alter enzymatic activity as well as enzyme chimeras or fusions with other polypeptide sequences.

While the proteins of Group 4 are not enzymes, for ease of discussion, references to "enzymes" herein are intended to encompass proteins of Group 4.

Which combination of enzymes are employed will depend on, for example, the cellulose source, type of pre-treatment (if any) of cellulosic material and the temperature and pH of the fermenter reaction. Combinations that include enzymes of Group 4 are of particular use for degrading a cellulosic source. In general, proteins of Group 4 will be most effective when the particular Group 4 protein is from the same plant genus or species as the source of cellulose. Thus, for example, where the cellulose source is from rice plants, the most effective expansin or swollenin is a rice expansin or swollenin (e.g., expressed from yeast). Expansins from a wide variety of plants are known, and include expansins from *Populus trichocarpa, Rumex acetosa Rumex palustra, Brassica, Gossypium, Pinus taeda, Nicotiana, Prunus armeniaca, Zea mays, Glycine, Holcus, Oryza, Phalaris, Poa pretense* and *Tricicum aestivum*.

In some embodiments, the combinations of enzymes include at least an enzyme from Group 4 and an enzyme from either Group 2, 3, 5, and/or 6. For example, in some embodiments, the combination includes at least one enzyme from Group 4 (i.e., an expansin or swollenin) and an enzyme from Group 2 (i.e., a cellulase or a glucosidase) or 5 (i.e., a feruloyl esterase, a lipase or a cutinase). In some embodiments, the combination includes at least three enzymes comprising: at least one enzyme from Group 4 and at least one enzyme from each of Group 2 and 5.

In some embodiments, the combinations of enzymes include at least an enzyme from Group 4 and at least one enzyme from each of groups 2 and 3. In some embodiments, for example, the combination of enzymes includes at least one non-glucanase cellulase, a glucanase (e.g., beta-glucanase), and a xylanase.

In some embodiments, the combination of enzymes includes at least one enzyme from Group 1 (i.e., an amylase) and at least one enzyme from Group 3 (i.e., a xylanase) or Group 6 (i.e., a ligninase or laccase). In some embodiments, the combination of enzymes includes at least one enzyme from Group 1 and at least one enzyme from Group 3 and Group 6. Combinations described in this paragraph are useful for converting cornstarch-based feedstocks as well as cellulose sources into free sugars. These combinations are particularly advantageous when expressed from a yeast strain that consumes or produces only minimal glycerin, thereby resulting in a saccharification process with greatly reduced glycerin and fiber content, and increasing ethanol yields.

In some embodiments, the combination of proteins includes at least four proteins, each selected from a different group in Table 1, optionally wherein one of the proteins is from group 4. In some embodiments, the combination of proteins includes at least five proteins, each selected from a different group in Table 1, optionally wherein one of the proteins is from group 4. In some embodiments of the invention, the combination of enzymes includes at least one enzyme from each of Groups 1, 2, 3, 4, 5, and 6.

In any of the combinations described herein, one can optionally further include more than one protein from a particular group. For example, in some embodiments, the combinations include at least two enzymes of Group 2, optionally each having a different activity (e.g., an endoglucanase and a second cellulase that is not an endoglucanase).

III. Yeast

As described herein, in some embodiments, the enzymes of the invention are expressed in one or more yeast strain. Any yeast strain can be used according to the present invention. Yeast are unicellular microorganisms that belong to one of three classes: *Ascomycetes, Basidiomycetes* and *Fungi Imperfecti*. While pathogenic yeast strains, or nonpathogenic mutants thereof, can be used in accordance with the present invention, nonpathogenic yeast strains will generally be used. Exemplary genera of yeast strains include *Saccharomyces, Candida, Cryptococcus, Hansenula, Kluyveromyces, Pichia, Rhodotorula, Schizosaccharomyces* and *Yarrowia*. Exemplary species of yeast strains include *Saccharomyces cerevisiae, Saccharomyces carlsbergensis, Candida albicans, Candida kefyr, Candida tropicalis, Cryptococcus laurentii, Cryptococcus neoformans, Hansenula anomala, Hansenula polymorpha, Kluyveromyces fragilis, Kluyveromyces lactis, Kluyveromyces marxianus* var. *lactis, Pichia pastoris, Rhodotorula rubra, Schizosaccharomyces pombe*, and *Yarrowia lipolytica*. It is to be appreciated that a number of these species include a variety of subspecies, types, subtypes, etc. that are meant to be included within the aforementioned species. In some embodiments of the present invention, a yeast strain capable of replicating plasmids to a particularly high copy number is used.

The synthetic expression cassettes constructed through the methods described herein may be recombinantly expressed by molecular cloning into an expression vector containing a suitable promoter and other appropriate transcription regulatory elements, and transferred into prokaryotic or eukaryotic host cells to produce recombinant enzymes. Techniques for such manipulations are fully described by Sambrook et al. (Molecular Cloning: A Laboratory Manual; Cold Spring Harbor Laboratory, Cold Spring Harbor, N.Y., (1989); Current Protocols in Molecular Biology, Ausubel et al., Green Pub. Associates and Wiley-Interscience, New York (1988); Yeast Genetics: A Laboratory Course Manual, Rose et al., Cold Spring Harbor Laboratory, Cold Spring Harbor, N.Y., (1990)).

A variety of techniques are available and known to those skilled in the art for introduction of nucleic acid constructs into a cellular host. Transformation of microbial cells may be accomplished through, e.g., use of polyethylene glycol, calcium chloride, viral infection, DEAE dextran, phage infection, electroporation and other methods known in the art. Transformation of fungus, in particular *Pichia*, may be accomplished, for example, according to "*Pichia* Protocols", in *Methods Mol. Biol.*, Higgins, David R. and Cregg, James M.; Eds. (Humana, Totowa, N.J.) (1998). Introduction of the recombinant vector into yeasts can be accomplished by methods including electroporation, use of spheroplasts, lithium acetate, and the like.

The present invention provides for yeast strains that express one or more proteins of the invention. For example, a single yeast cell can be engineered to express one, two, three or more different proteins. While it can be beneficial to express more than one protein in a single yeast strain, overall protein production (e.g., units of activity, overall quantity of protein, etc.) can be degraded if too many different proteins are produced from a single strain. Therefore, in some embodiments, the invention provides for one two or three proteins produced from a single yeast strain. If additional proteins are desired in a combination in a culture, in some embodiments, a second (or third, fourth, etc.) yeast strain is provided that expresses one or more additional protein. Thus, the present invention provides for isolated yeast strains as well as cultures (i.e., solutions comprising yeast cells that express the proteins, optionally where the cells divide and multiply) of combinations of yeast strains.

Those of skill in the art will appreciate that a combination of proteins can be produced in several ways. The following list is merely provided as an example and is not intended to be an exhaustive list of possible combinations.

Two proteins: (1) two yeast strains, each producing one of the proteins; (2) one yeast strain producing both proteins.

Three proteins: (1) three yeast strains, each producing one of the proteins; (2) one yeast strain producing two proteins, and a second yeast strain producing the third protein; (3) one yeast strain producing three proteins.

Four proteins: (1) four yeast strains, each producing one of the proteins; (2) two yeast strains, each producing two proteins, (3) two yeast strains, one strain producing three proteins and the second strain producing one protein; (4) three yeast strains, two strains each producing one enzyme and the third protein producing the two remaining enzymes, (5) one yeast strain producing four proteins.

Five proteins: (1) five yeast strains, each producing one of the proteins; (2) two yeast strains, each producing two proteins, plus a third strain producing the fifth protein; (3) two yeast strains, one strain producing three proteins and the second strain producing the two remaining proteins; (4) four yeast strains, one strain producing two proteins, and three strains each producing one protein; (5) three yeast strains, one producing three proteins, and two that each produce one protein.

Six proteins: (1) Six yeast strains, each producing one of the proteins; (2) three yeast strains, each producing two proteins; (3) two yeast strains, each producing three proteins. Other options include, e.g., 4/2, 3/2/1, 3/1/1/1/, 4/1/1, etc.

Yeast expressing one or more protein of the invention can be generated as is known in the art. For example, expression cassettes comprising a promoter operably linked to a coding sequence for proteins of the invention as described herein can be (optionally inserted into a nucleic acid vector and) introduced into the yeast. A number of expression vectors for various yeast species are known in the art and some can be obtained commercially. Vectors can optionally include an origin of replication and/or a marker gene for identifying cells transformed with the vector. In some embodiments, the expression cassettes are stably introduced into a yeast chromosome or extrachromosomal DNA.

Any number of promoters can be used to drive expression from the expression cassettes of the invention. Exemplary promoters include, e.g., constitutive or inducible promoters. Recombinant gene expression can be driven by promoters including, but not limited to, the yeast GAL10 gene promoter, the phosphoglycerate kinase (PGK) promoter (see, e.g., Tuite, M. F. et. al. (1982) *EMBO Journal* 1, 603-608.; WO 84/04757), GAL10/PGK promoter chimeras (see, e.g., U.S. Pat. No. 5,739,007) or other yeast promoters such as alcohol dehydrogenase (see, e.g., Bennetzen, J. L. and Hall, B. D. *J. Biol. Chem.* 257:3018 (1982); Ammerer, G. in *Methods in Enzymology Vol.* 101, p. 192 (1983)) phosphoglycerate kinase (see, e.g., Derynck, R., Hitzemann, R. A., Gray, P. W., Goeddel, D. V., in *Experimental Manipulation of Gene Expression*, 1983, p. 247, ed. M. Inouye, Academic Press), triose phosphate isomerase (see, e.g., Alber, T. and Kawasaki, G., *J. Molec and Applied Genet.* 1: 419-434 (1982)), or enolase (see, e.g., Innes, M. A. et al. *Science* 226:21 (1985)) can be used in a similar manner. The invention herein provides a method to excrete proteins into a cellulose source (e.g., a fermentation "mash") at a balanced rate of production that uniquely controls the rate of fermentation by control of enzyme expression By the careful selection of promoters driving expression of the enzymes, the level of protein production can be gated, permitting fermentations to proceed at measured or controlled rates. In other words, the rate of sugar production is controlled by release of enzymes.

Expression vectors used in yeast cells can also contain sequences necessary for the termination of transcription and for stabilizing the mRNA. Such sequences are commonly available from 3' to the translation termination codon, in untranslated regions of eukaryotic or viral DNAs or cDNAs. These regions contain nucleotide segments transcribed as polyadenylated fragments in the untranslated portion of the mRNA.

Yeast cells can be engineered to secrete the proteins of the invention or optionally can be engineered such that the proteins are active and attached to the surface of the yeast cells. A variety of methods are known for secretion of heterologous proteins from yeast. See, for example, US Patent Publication Nos. 2007/0077619 and 2006/0234351 and European Patent EP0256421. In some embodiments, secretion is achieved by inclusion of an appropriate signal sequence as a fusion with the enzyme. Exemplary signal sequences are described in the art, including not limited to, U.S. Pat. No. 5,521,086.

Optionally, one or more of the enzymes expressed from a yeast strain is attached to the surface to the yeast cell surface. In some embodiments, the proteins of the present invention are fused to α-agglutinin or a fragment thereof, resulting in surface expression. See, e.g., Murai et al., *Applied and Environmental Microbiology*, 64(12):4857-4861 (1998).

IV. Conversion of Cellulose to Sugars

The present invention provides for conversion of cellulose and other plant materials into sugars by employing the combinations of enzymes described herein. As demonstrated in the examples, combination of enzymes greatly increase conversion of cellulose into various sugars. Further, mixture of cellulose and other plant material (e.g., hemicellulose, lignins, etc.) with yeast expressing the enzyme combinations allows for efficient conversion of the plant material into sugars without costly purification of enzymes. Further, in some embodiments, the yeast also ferments the resulting sugar into alcohol (e.g., ethanol and/or butanol). This aspect is particularly advantageous because accumulation of sugars can in some instances act to inhibit the enzymes' activities. By fermenting the sugars into alcohols, the yeast increases the overall production and speed of conversion of cellulose and other plant materials into sugars and ultimately into alcohols. Thus, in some embodiments, the yeast of the invention express the proteins of the invention during fermentation and/or saccharification, and optionally such that saccharification and fermentation occur simultaneously.

It will be appreciated that a wide variety of plant material or other sources of cellulose can be used as a carbon source. Exemplary cellulose sources include, but are not limited to, all types of woods, distillers grains, sugar cane, rice straws, rice hulls, wheat straws, switchgrass, waste agricultural materials, sawdust, recycled building materials, papers, cardboard, composite boards, sludge, corn stover, whole corn, ground corn, corn silage, sorghum, energy cane and materials containing (e.g., over 5%) cellulose.

In some embodiments, the cellulose sources are added directly to the proteins of the invention (e.g., as expressed in yeast cultures/suspensions) to form an aqueous mixture and incubated under conditions to allow for efficient conversion of cellulose and other plant material to sugars. In some embodiments, cellulose source or plant material is first pre-treated to render the cellulose more available to the enzymes. In some embodiments, the material is ground into finer pieces or otherwise treated to increase surface area of the material. In some embodiments, the pre-treatment comprises at least one of the following: acid hydrolysis (see, e.g., U.S. Pat. Nos. 4,174,976 and 5,597,714; and PCT Publication WO/2006/086861), steam explosion (see, e.g., U.S. Pat. No. 6,506,282 and PCT Publication WO/2000/039387), autohydrolysis, ionic liquids (see, e.g., U.S. Pat. No. 6,824,599), hot water, ammonia explosion (see, e.g., U.S. Pat. No. 5,037,663), extrusion (see, e.g., U.S. Pat. No. 7,037,096;), or microwave treatment (see, e.g., U.S. Pat. No. 5,196,069).

Those of skill in the art will appreciate that different pre-treatments will result in different pHs of the resulting pre-treated cellulose material. Thus, the greatest enzymatic activity will be achieved by selecting enzymes which act at the pH of the pre-treated material. For example, if acid hydrolysis is used, it will be beneficial to selected a cellulase, beta-glunanase, and/or xylanase (or other enzyme/protein) that has an optimal performance at a lower pH. If ammonia explosion is used, an enzyme with an optimal performance at a higher pH can be selected. In some embodiments, the cellulose material is pre-treated with heat (e.g., greater than 100° C.) in the presence of a room temperature ionic liquid (RTIL), e.g., an aqueous liquid comprising acetate such as EMIM acetate in an amount sufficient to reduce the crystallinity of the material.

Yeast can be grown as appropriate. For example, yeast expressing the proteins described herein can be grown, e.g., from particular slants and propagated from, e.g., a 250 ml shaker flask to a 20 L carboy, then, e.g., to a 1600 L reactor and finally to, e.g., a 160,000 L propagator. In some embodiments, inoculums of 2-10% of the production volume of the commercial fermenter are used. The initial yeast concentration in the fermenter can be, for example, greater than $10^4$ CFU/ml. Optionally, the yeast can be dried into active dry yeast. In some embodiments, the dry yeast can be propagated in a, e.g., 16,000 L reactor then a, e.g., 160,000 L propagator. This yeast propagator can be supplied in inoculums of, e.g., 2-10% of the production volume of the commercial fermenter.

The proteins and cellulose material (and optionally yeast cells expressing the proteins) can be incubated in any way that is convenient for industrial operations. The process can be performed, for example, in a batch-wise or continuous flow process. A continuous flow process can include continued addition of nutrients, yeast, and/or cellulose material with removal of solids, sugars, alcohols or other products as appropriate. The mixture can be optionally actively mixed or otherwise aerated.

In some embodiments, fermentation temperatures will be controlled between 28-35° C. and pH 4.0-5.5. There are other factors affecting enzyme activity include surface area, pore volume, pore size distribution of the cellulosic materials, pretreatment method, the presence or absence of enzyme inhibitors such as furfurals, and the presence of various enzymecofactors. Many enzymes require the presence of an additional, nonprotein, cofactor. Some of these are metal ions such as $Ca^{2+}$, $Zn^{2+}$, $Cu^{2+}$, $Mn^{2+}$, $K^+$, and $Na^+$, which are commonly present in biomass. In some embodiments, ligninases will specifically require manganese for generation of hydrogen peroxide. Some cofactors are small organic molecules called coenzymes. The B vitamins thiamine (B1), riboflavin (B2) and nicotinamide are precursors of some coenzymes. Coenzymes may be covalently bound to the protein part (called the apoenzyme) of enzymes as a prosthetic group. Others bind more loosely and, in fact, may bind only transiently to the enzyme as it performs its catalytic act. These are normally present in enough concentration in typical fermentations, however if they are deficient, they can be added to the fermenter in order to enhance the conversion.

In some embodiments, cellulosic materials can be used as an inexpensive form of sugar (i.e., for value added products). In some of these embodiments, excess sugar is bled from the saccharification tank(s) (i.e., where the enzymes are converting plant material to sugar), for example using a sequential membrane, filtrate wash, or other sugar removal system. This reduces the sugar concentration in the saccharification tank(s) and allows for hydrolysis to continue without being inhibited by excess sugar. Residual non-sugar producing solids can be optionally purged forward for further processing or for other uses (such as for fuel value in a cogeneration system).

Furfurals can accumulate in some saccharification reactions. Furfurals can in some embodiments act as yeast growth inhibitors. Thus, bacteria that consume furfurals can also be added to the fermentation to selectively reduce or eliminate the furfurals.

Microbial contamination can be reduced or eliminated in the mixture by use of antibiotics or other microbial growth inhibitors (e.g., peroxide). Alternatively, inclusion of yeast strains that express ligninases or other enzymes from Group 6 can result in hydrogen peroxide production, thereby reducing of eliminating the need to exogenous addition of peroxides.

In some embodiments, the mixture of yeast cells and cellulose material are incubated to result in production of sugars from cellulose or other plant material and subsequent fermentation of the sugars into alcohols. Industrial fermentation conditions are known in the art. A modified form of Simultaneous Saccharification and Fermentation (SSF) can be accomplished by using a small saccharification step in order to produce a small amount of sugar to promote yeast growth. This partially converted media is then sent to the fermenter. After the fermenter volume is approximately 10-20% of the total fermenter volume the yeast inoculum is added. The tank is then continuously filled in a fed batch mode over a period of 25-35 hours and then held at 35° C. until the fermentation is complete (~72 hrs). This allows sufficient use of the sugars to prevent inhibition of the process. To improve alcohol production, yeast strains with a high ethanol tolerance can be selected.

Yeast growth stimulants can also be added to the mixture. For example, sterols can be added to stimulate yeast growth and enzyme production.

The yeasts of this invention are exceptionally efficient for the production of ethanol. However, some of the same yeasts can be used for saccharification without subsequent fermentation. This can be accomplished, for example, by, e.g., allowing the yeasts to generate biomass, limiting ethanol production, followed by deactivation of the yeast so the fluid contains free enzymes and proteins, or in the case of the surface engineered yeasts the yeasts can be cultivated, deactivated with ultrasound and then used as immobilized enzymes within the saccharification vessel. They can be filtered at the end of the saccharification process along with the other solids in this manner. A large market for these types of yeasts are ones that have the ethanol pathway blocked and make only sugars. This is applicable when making polymers or high molecular weight biofuels rather than for ethanol production.

EXAMPLES

The following examples are offered to illustrate, but not to limit the claimed invention.

Example 1

This example describes experiments showing improved production of sugars from cellulose sources using combinations of enzymes compared to single enzyme treatments.

The core instruments used in the experiments described herein were a Waters HPLC used to analyze for glucose, xylose, arabinose and total sugars. To measure residual solids, an IR balance was used. In some cases, additional analyses was performed by various outside laboratories who specialize in quantitative measurements of cellulose, hemicelluloses, fiber, lignin and other components.

For the first set of experiments, dried distillers grains (DDG) were used from corn processing plants. These particles were milled to be minus 35 mesh size. The DDG was mixed with an acetate buffer at pH 4.5 and held at 55C in an incubator shaker for 48-120 hours. For each run, 50 ml to 100 ml of buffer was used with 2.5 gm to 10.0 gm of minus 35 mesh DDG. The total enzyme weight in each case was 0.5% by weight of the DDG. All experimental results were corrected for DDG concentration. All HPLC data used calibration solutions before during and after the runs to insure accuracy on the data. The exposure times used for the enzymes once added to the acetate buffers were either 48 hours or 120 hours. In every case, to compare combinations of enzymes, solutions were held at the same temperature for the same times to make an equitable comparison on activity.

The following liquid commercial enzymes were used for this study. The enzymes combinations called out in Tables 3 and 4 correspond with the alpha character listed before each particular enzyme. Bolded numbers in the tables represent the highest yields reached for a particular sugar.

A: Novozyme 50013 (Cellulase);

B: Novozyme 50010 or 188 (Glucosidase);

C: Novozyme 50030 or 22030 (Xylanase);

X: Genencor GC 220 (Cellulase);

Y: Genencor SPEZYME CP (Cellulase);

Z: Genencor MULTIFECT (Xylanase)

TABLE 2

Individual Enzymes
Temperature: 55 C., Acetate buffer (pH: 4.5): 50 ml,
DDG (minus 35 sieve): 2.5 gm
Total Enzyme: 0.5% by DDG wt, total 120 hrs

|  | Glucose, g/g DDG | | Xylose, g/g DDG | | Total Sugar | |
| --- | --- | --- | --- | --- | --- | --- |
|  | 48 hrs | 120 hrs | 48 hrs | 120 hrs | 48 hrs | 120 hrs |
| 50013 (Cellulase) | 0.0295 | 0.0326 | 0.0026 | 0.0023 | 0.0321 | 0.0349 |
| 50010 (Glucosidase) | 0.0255 | 0.0288 | 0.0012 | 0.0012 | 0.0267 | 0.03 |
| 50030 (Xylanase) | 0.0133 | 0.0152 | 0.0032 | 0.0035 | 0.0165 | 0.0187 |
| GC 220 (Cellulase) | 0.0292 | 0.0325 | 0.0015 | 0.0013 | 0.0307 | 0.0338 |
| SPEZYME (Cellulase) | 0.0262 | 0.0321 | 0.0018 | 0.0016 | 0.0279 | 0.0337 |
| MULTIFECT (Xylanase) | 0.0211 | 0.0248 | 0.002 | 0.0018 | 0.023 | 0.0266 |
| CONTROL |  | 0.0016 |  | 0.0026 |  | 0.0041 |

TABLE 3

Enzyme Pairs
Temperature: 55 C., Acetate buffer (pH: 4.5): 50 ml,
DDG (minus 35 sieve distillers grain): 2.5 gm
Total Enzyme dosage: 0.5% by DDG wt (0.25% each)

| | | g/g DDG | | | |
|---|---|---|---|---|---|
| Time, hr | Enzyme | Glucose | Xylose | Arabinose | Total |
| 140 | A + C | 0.0347 | 0.0019 | 0.0027 | 0.0393 |
| 140 | A + X | 0.0427 | 0.0021 | 0.0034 | 0.0483 |
| 140 | A + Y | 0.0033 | 0.0034 | 0.0020 | 0.0087 |
| 140 | A + Z | 0.0377 | 0.0022 | 0.0031 | 0.0430 |
| 140 | C + X | 0.0418 | 0.0015 | 0.0037 | 0.0470 |
| 140 | C + Y | 0.0330 | 0.0013 | 0.0031 | 0.0373 |
| 140 | C + Z | 0.0275 | 0.0018 | 0.0033 | 0.0327 |
| 140 | X + Y | 0.0385 | 0.0017 | 0.0035 | 0.0437 |
| 140 | X + Z | 0.0374 | 0.0017 | 0.0035 | 0.0426 |
| 140 | Y + Z | 0.0160 | 0.0026 | 0.0052 | 0.0237 |
| 140 | Control | 0.0023 | 0.0033 | 0.0032 | 0.0087 |
| 72 | A + B | 0.0445 | 0.0019 | 0.0046 | 0.0509 |
| 72 | B + C | 0.0306 | 0.0014 | 0.0042 | 0.0362 |
| 72 | B + X | 0.0432 | 0.0013 | 0.0054 | 0.0498 |
| 72 | B + Y | 0.0379 | 0.0014 | 0.0045 | 0.0438 |
| 72 | B + Z | 0.0313 | 0.0014 | 0.0047 | 0.0375 |

These initial experiments demonstrated that the appropriate combination of enzymes can make a difference of a factor of two or three compared to using the same concentration of a single enzyme or compared to other combinations of enzymes. Furthermore it demonstrates the importance of choosing enzymes having different activities.

Starting with these initial experiments, further work was done to determine how to choose or select fruitful combinations. After many experiments, the set of enzymes and proteins available to assist in saccharification were divided into finite categories as shown in Table 4. This grouping of enzymes for converting cellulose material into sugars provides a powerful guide for enzyme selection. Further, these groupings provide a guide for how to select more efficient enzyme blends expressed in yeast.

TABLE 4

Higher Combinations
DDG (minus 35 sieve distillers grain): 10 gm Acetate buffer (pH: 4.5): 100 ml
Each Enzyme dosage: 0.5% by DDG wt

| | | g/g DDG | | | |
|---|---|---|---|---|---|
| Total Enzyme load, % of DDG | Enzymes | Glucose | Xylose | Arabinose | Total |
| Temp 55 C. 72 hrs | | | | | |
| 1.5 | A + X + Y | 0.0463 | 0.0015 | 0.0033 | 0.0511 |
| 1.5 | A + X + Z | 0.0490 | 0.0015 | 0.0033 | 0.0538 |
| 1.5 | A + Y + Z | 0.0420 | 0.0010 | 0.0034 | 0.0464 |
| 1.5 | B + X + Y | 0.0509 | 0.0050 | 0.0074 | 0.0633 |
| 1.5 | B + X + Z | 0.0500 | 0.0049 | 0.0074 | 0.0623 |
| 1.5 | B + Y + Z | 0.0456 | 0.0041 | 0.0073 | 0.0570 |
| 1.5 | C + X + Y | 0.0439 | 0.0000 | 0.0033 | 0.0471 |
| 1.5 | C + X + Z | 0.0457 | 0.0000 | 0.0031 | 0.0489 |
| 1.5 | C + Y + Z | 0.0363 | 0.0012 | 0.0036 | 0.0411 |
| Temp 55 C. 85 hrs | | | | | |
| 1.5 | X + Y + Z | 0.0413 | 0.0008 | 0.0038 | 0.0459 |
| 1.5 | A + B + C | 0.0482 | 0.0043 | 0.0057 | 0.0582 |
| 2 | X + Y + Z + A | 0.0462 | 0.0011 | 0.0038 | 0.0511 |
| 2 | X + Y + Z + B | 0.0454 | 0.0041 | 0.0070 | 0.0565 |
| 2 | X + Y + Z + C | 0.0412 | 0.0010 | 0.0037 | 0.0459 |
| 2.5 | X + Y + Z + A + B | 0.0521 | 0.0048 | 0.0075 | 0.0644 |
| 2.5 | X + Y + Z + A + C | 0.0445 | 0.0012 | 0.0037 | 0.0493 |

Example 2

This example describes a proposed treatment to obtain ethanol from rice straw.

A strain of *Saccharomyces cerevisiae* is used that has been selected for low glycerin production. The strain is recombinantly engineered to express three proteins, one each from Groups 2, 4 and 5 of Table 1. This combination is used with rice straw that has been pre-treated using a co-current auto-hydrolysis extrusion method. The yeast is added to the extrudate at a level of 1 kg per 1000 kg of treated rice straw at 25% solids. The conversion of the rice straw to ethanol based on the available sugar content is 45%.

Example 3

This example describes a different proposed treatment to obtain ethanol from rice straw.

A strain identical to that used in Example 2 is used. In this example, The strain is recombinantly engineered to express three proteins, one each from Groups 1, 3 and 6 of Table 1. This yeast is combined with the rice straw prepared as described in Example 2. In this example, 0.5 kg of each yeast is used instead of 1 kg. The combined conversion to ethanol based on the sugar content as determined by cellulose and hemicellulose assays is 75%.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

SEQUENCE LISTING

SEQ ID NO: 1
AAB81662
MAIAG--VLFLLF-----LAR-----------QASAAGYGGWQSAHATF
YGGGDASGT--MGGACGYGNLYSQGYGTNTAALSTALFNDGAACGSCYEL
RCDNAGSS-CLPGSITVTATNFCPPNYGLPSDDGGWCNPPRPHFDMAEPA
FLHIAQYRAGIVPVSFRRVPCVKKGG--IRFTVNG--HSYFNLVLVTNVA
GAGDVRSVSIKGSR-TGWQPMSRNWGQNWQSNAFLDGQ-SLSFQVTASDG
RTVTSNNVAHPGWQFGQTFEG-GQF-

SEQ ID NO: 2
NP 001105040
MAAAASALLLLLCSAFCSLAH-----------RAAGVDYGSWQSAHATF
YGGGDASGT--MGGACGYGNMYSTGYGTNTAALSTALFNDGAACGSCYEL
RCDNNGQS-CLPGTITVTATNFCPPNYGLPSDDGGWCNPPRPHFDMAQPA
FLQIAQYRAGIVPVAYRRVPCVKKGG--IRFTING--HSYFNLVLVTNVA
GAGDVQSVSIKGSS-TGWQPMSRNWGQNWQSNSLLDGQ-SLSFQVTASDG
RTVTSNGVAPAGWQFGQTFEG-AQF-

SEQ ID NO: 3
BAC66786
MK-MALAYGFCLVGLLAMVS-------------CAHAYGGGWVNARATF
YGGGDASGT--MGGACGYGNLYSQGYGTNTAALSTALFNNGLGCGSCYEI
RCVSDPKW-CLPGAIVVTATNFCPPNNALPNNAGGWCNPPLHFDLSQPV
FQHIAQYKAGVVPVAYRRVPCRRRGG--IRFTING--HSYFNLVLITNVG
GAGDVHSVSVKGSR-TGWQAMSRNWGQNWQSNSYLNGQ-SLSFKVTTSDG
RTVVSYNAAPAGWSFGQTYSG-AQFR

SEQ ID NO: 4
AAD47901
MRSMELVKSIALASLLTFIWL-----------LTGAHGYGGWESAHATF
YGGSDASGT--MGGACGYGNLYSQGYGTNTAALSTALFNDGLSCGACYEM
RCNDDPQW-CLPGTVTVTATNFCPPNNALPNDNGGWCNPPLQHFDMAEPA
FLKIAKYRGGIVPILYTRVPCLRKGG--IRFTVNG--HSYFNLVLITNVG
GAGDVHAVSIKGSR-SGWQPMSRNWGQNWQSNSYLNGQ-SLSFQVTTSDG
RTVVSNNVAPSNWQFGQTFEG-SQV-

SEQ ID NO: 5
Alpha expansin consensus sequence
GXWXXAXATFYGGXDASGTXXMGGACGYGNXYSXGYGTNTAALSTALFNX
GXXCGXCYEXRCXXXXXXXCLPGXXXVTATNFCPXXXGGXXIRFTXNGXXHSY
XXHFDXXXPXFXXIAXYXXGXVPXXXXRVPCXXXGGXXIRFTXNGXXSY
FNLVLXTNVXGAGDVXXVSXKGSXXXGWQMSRNWGQNWQSNXXLXGQXS
LSFXVTXSDGRTVXSXXXAXXXWXFGQTXXGXXQ SEQ ID NO: 6
AAS21274
MGSVS--YVLAAAVLAALVSGGACIP-KVPPGPNITTNYNNQWLSAKATW
YGRPTGSGPKDNGGACGIKDVNLAPYNGMIACGNVPIFKDGKGCGSCYEI KCQKPSP-CSDKPITIFITDKNYEPIAPYHIDLSGTAFGAMATPGKEQTL
SRFGELELQFRRVRCKYAPGTKITFHVEKGSNPNYLAVLVKFVSDDGDVV
QMDIQESKSPAWIPLTLSWGAIWRWDGAKPLKGPFSIRVTSESGKKLIAK
DVIPANWKADTVYTSNVQF- SEQ ID NO: 7
AC087676
MASSK--MMLAMAVLAALLSLAHGIP-KVPPGPNITATYNGKWLDAKSTW
YGRPEGAGPKDNGGACGYKDVDKPPFNGMTSCGNTPIFRDGRGCGSCFEV
KCEKPAEFCSGQPVLVHITDDNEEPIAAYHFDLSGKAFGSMAKKGQEQKL
RGCGEVEIQFRRVKCYYPLGTKVTYHVEKGSNPNYLALLVKFVGGDGDVV
AVEVQEKGKYNWIPLKESWGAVWRIDTAKPLKGPLSVRYTTDGGTKAVSP
DVIPEKWKPDTMYVAKY---

SEQ ID NO: 8
NP 001065305
MGSLTTNIVLAVAVVAALVGGGSCGPPKVPPGPNITTNYNAPWLPARATW
YGQPYGSGSTDNGGACGIKNVNLPPYNGMISCGNVPIFKDGRGCGSCYEV
KCEQPAA-CSKQPVTVFITDMNYEPISAYHFDFSGKAFGAMACPGKETEL
RKAGIIDMQFRRVRCKYPGGQKVTFHVEKGSNPNYLAVLVKFVADDGDVI
QMDLQEAGLPAWRPMKLSWGAIWRMDTATPLKAPFSIRVTTESGKSLIAK
DVIPVNWMPDAIYVSNVQFY

SEQ ID NO: 9
NP 001105209
MGSLANNIMVVGAVLAALVVGGSCGPPKVPPGPNITTNYNGKWLTARATW
YGQPNGAGAPDNGGACGIKNVNLPPYSGMTACGNVPIFKDGKGCGSCYEV
RCKEKPE-CSGNPVTVFITDMNYEPIAPYHFDLSGKAFGSLAKPGLNDKL
RHCGIMDVEFRRVRCKYPAGQKIVFHIEKGCNPNYVAVLVKFVADDGDIV
LMEIQDKLSAEWKPMKLSWGAIWRMDTAKALKGPFSIRLTSESGKKVIAK
DIIPANWRPDAVYTSNVQFY

SEQ ID NO: 10
Beta expansin amino portion consensus sequence
KVPPGPNITXXYNXXWLXAXXTWYGXPXGXGXXDNGGACGXKXVXXXPXX
GMXXCGNXPIFXDGXGCGSCXEXXC SEQ ID NO: 11
Beta expansin carboxyl portion consensus sequence
CSXXPXXXXITDXNXEPIXXYHXDXSGXAFGXXAXXGXXXXLRXXGXXXX
XFRRVXCXYXXGXKXXXHXEKGXNPNYXAXLVKFVXXDGDXXXXXXQXXX
XXXWXPXXXSWGAXWRXDXAXXLKXPXSXRXTXXXGXXXXXXDXIPXXWX
XDXXY Dashes are merely included for alignment and do not represent
an amino acid position; X represents any amino acid.

What is claimed is:

1. An isolated yeast cell that heterologously expresses the following proteins:
   (a) an expansin comprising the polypeptide sequence of SEQ ID NO:5; and
   (b) a glucosidase, and
   (c) a laccase.

2. The isolated yeast cell of claim 1, wherein the yeast cell further expresses a beta expansin.

3. The isolated yeast cell of claim 1, wherein the proteins are secreted outside the yeast cell.

4. The isolated yeast cell of claim 1, wherein the proteins are linked to the yeast cell wall or cell membrane.

5. The isolated yeast cell of claim 1, wherein the yeast is selected from the group consisting of *Saccharomyces* ssp., *Schizosaccharomyces* ssp., *Candida* ssp., *Cryptococcus* ssp., *Hansenula* ssp., *Kluyveromyces* ssp. and *Pichia* ssp.

6. A cell culture comprising the yeast cell of claim 1, further comprising a source of cellulose.

7. The cell culture of claim 6, wherein the concentration of yeast cells is at least $10^5$ cfu/ml.

8. A method of converting a source of cellulose into sugars, the method comprising:
   (a) incubating the source of cellulose in an aqueous medium with a culture of the yeast of claim 1 for a sufficient length of time to convert the cellulose in the source into sugars.

9. The method of claim 8, wherein the source of cellulose is at least 5% cellulose.

10. The method of claim 8, wherein the source of cellulose is selected from the group consisting of wood, distillers grain, sugar cane, rice straw, rice hulls, wheat straw, switchgrass, waste agricultural material, sawdust, recycled building materials, paper, cardboard, composite board, sludge, corn stover, whole corn, ground corn, corn silage, sorghum, and energy cane.

11. The method of claim 8, wherein the sugar formed by the method is fermented by the yeast to produce alcohols.

12. The method of claim 8, wherein the concentration of yeast cells is at least $10^5$ cfu/ml.

* * * * *

SEQUENCE LISTING

<160> NUMBER OF SEQ ID NOS: 23

<210> SEQ ID NO 1
<211> LENGTH: 246
<212> TYPE: PRT
<213> ORGANISM: Oryza sativa
<220> FEATURE:
<223> OTHER INFORMATION: Oryza sativa Indica Group strain Pin Gaew 56
      deep water rice expansin (Os-EXP4)

<400> SEQUENCE: 1

Met Ala Ile Ala Gly Val Leu Phe Leu Leu Phe Leu Ala Arg Gln Ala
1               5                   10                  15

Ser Ala Ala Gly Tyr Gly Gly Trp Gln Ser Ala His Ala Thr Phe Tyr
            20                  25                  30

Gly Gly Gly Asp Ala Ser Gly Thr Met Gly Gly Ala Cys Gly Tyr Gly
        35                  40                  45

Asn Leu Tyr Ser Gln Gly Tyr Gly Thr Asn Thr Ala Ala Leu Ser Thr
    50                  55                  60

```
Ala Leu Phe Asn Asp Gly Ala Ala Cys Gly Ser Cys Tyr Glu Leu Arg
 65                  70                  75                  80

Cys Asp Asn Ala Gly Ser Ser Cys Leu Pro Gly Ser Ile Thr Val Thr
                 85                  90                  95

Ala Thr Asn Phe Cys Pro Pro Asn Tyr Gly Leu Pro Ser Asp Asp Gly
            100                 105                 110

Gly Trp Cys Asn Pro Pro Arg Pro His Phe Asp Met Ala Glu Pro Ala
            115                 120                 125

Phe Leu His Ile Ala Gln Tyr Arg Ala Gly Ile Val Pro Val Ser Phe
            130                 135                 140

Arg Arg Val Pro Cys Val Lys Lys Gly Gly Ile Arg Phe Thr Val Asn
145                 150                 155                 160

Gly His Ser Tyr Phe Asn Leu Val Leu Val Thr Asn Val Ala Gly Ala
                165                 170                 175

Gly Asp Val Arg Ser Val Ser Ile Lys Gly Ser Arg Thr Gly Trp Gln
            180                 185                 190

Pro Met Ser Arg Asn Trp Gly Gln Asn Trp Gln Ser Asn Ala Phe Leu
            195                 200                 205

Asp Gly Gln Ser Leu Ser Phe Gln Val Thr Ala Ser Asp Gly Arg Thr
            210                 215                 220

Val Thr Ser Asn Asn Val Ala His Pro Gly Trp Gln Phe Gly Gln Thr
225                 230                 235                 240

Phe Glu Gly Gly Gln Phe
                245

<210> SEQ ID NO 2
<211> LENGTH: 253
<212> TYPE: PRT
<213> ORGANISM: Zea mays
<220> FEATURE:
<223> OTHER INFORMATION: Zea mays maize alpha expansin 1 (Exp1)

<400> SEQUENCE: 2

Met Ala Ala Ala Ser Ala Leu Leu Leu Leu Leu Cys Ser Ala Phe
 1               5                  10                  15

Cys Ser Leu Ala His Arg Ala Ala Gly Val Asp Tyr Gly Ser Trp Gln
                 20                  25                  30

Ser Ala His Ala Thr Phe Tyr Gly Gly Gly Asp Ala Ser Gly Thr Met
             35                  40                  45

Gly Gly Ala Cys Gly Tyr Gly Asn Met Tyr Ser Thr Gly Tyr Gly Thr
         50                  55                  60

Asn Thr Ala Ala Leu Ser Thr Ala Leu Phe Asn Asp Gly Ala Ala Cys
 65                  70                  75                  80

Gly Ser Cys Tyr Glu Leu Arg Cys Asp Asn Asn Gly Gln Ser Cys Leu
                 85                  90                  95

Pro Gly Thr Ile Thr Val Thr Ala Thr Asn Phe Cys Pro Pro Asn Tyr
            100                 105                 110

Gly Leu Pro Ser Asp Asp Gly Gly Trp Cys Asn Pro Pro Arg Pro His
            115                 120                 125

Phe Asp Met Ala Gln Pro Ala Phe Leu Gln Ile Ala Gln Tyr Arg Ala
            130                 135                 140

Gly Ile Val Pro Val Ala Tyr Arg Arg Val Pro Cys Val Lys Lys Gly
145                 150                 155                 160

Gly Ile Arg Phe Thr Ile Asn Gly His Ser Tyr Phe Asn Leu Val Leu
                165                 170                 175
```

-continued

Val Thr Asn Val Ala Gly Ala Gly Asp Val Gln Ser Val Ser Ile Lys
            180                 185                 190

Gly Ser Ser Thr Gly Trp Gln Pro Met Ser Arg Asn Trp Gly Gln Asn
        195                 200                 205

Trp Gln Ser Asn Ser Leu Leu Asp Gly Gln Ser Leu Ser Phe Gln Val
    210                 215                 220

Thr Ala Ser Asp Gly Arg Thr Val Thr Ser Asn Gly Val Ala Pro Ala
225                 230                 235                 240

Gly Trp Gln Phe Gly Gln Thr Phe Glu Gly Ala Gln Phe
                245                 250

<210> SEQ ID NO 3
<211> LENGTH: 252
<212> TYPE: PRT
<213> ORGANISM: Prunus persica
<220> FEATURE:
<223> OTHER INFORMATION: Prunus persica cultivar Akatsuki peach expansin
      (PpExp2)

<400> SEQUENCE: 3

Met Lys Met Ala Leu Ala Tyr Gly Phe Cys Leu Val Gly Leu Leu Ala
1               5                   10                  15

Met Val Ser Cys Ala His Ala Tyr Gly Gly Gly Trp Val Asn Ala
            20                  25                  30

Arg Ala Thr Phe Tyr Gly Gly Asp Ala Ser Gly Thr Met Gly Gly
            35                  40                  45

Ala Cys Gly Tyr Gly Asn Leu Tyr Ser Gln Gly Tyr Gly Thr Asn Thr
            50                  55                  60

Ala Ala Leu Ser Thr Ala Leu Phe Asn Asn Gly Leu Gly Cys Gly Ser
65                  70                  75                  80

Cys Tyr Glu Ile Arg Cys Val Ser Asp Pro Lys Trp Cys Leu Pro Gly
                85                  90                  95

Ala Ile Val Val Thr Ala Thr Asn Phe Cys Pro Pro Asn Asn Ala Leu
            100                 105                 110

Pro Asn Asn Ala Gly Gly Trp Cys Asn Pro Pro Gln His His Phe Asp
        115                 120                 125

Leu Ser Gln Pro Val Phe Gln His Ile Ala Gln Tyr Lys Ala Gly Val
    130                 135                 140

Val Pro Val Ala Tyr Arg Arg Val Pro Cys Arg Arg Gly Gly Ile
145                 150                 155                 160

Arg Phe Thr Ile Asn Gly His Ser Tyr Phe Asn Leu Val Leu Ile Thr
                165                 170                 175

Asn Val Gly Gly Ala Gly Asp Val His Ser Val Ser Val Lys Gly Ser
            180                 185                 190

Arg Thr Gly Trp Gln Ala Met Ser Arg Asn Trp Gly Gln Asn Trp Gln
        195                 200                 205

Ser Asn Ser Tyr Leu Asn Gly Gln Ser Leu Ser Phe Lys Val Thr Thr
    210                 215                 220

Ser Asp Gly Arg Thr Val Val Ser Tyr Asn Ala Ala Pro Ala Gly Trp
225                 230                 235                 240

Ser Phe Gly Gln Thr Tyr Ser Gly Ala Gln Phe Arg
                245                 250

<210> SEQ ID NO 4
<211> LENGTH: 253
<212> TYPE: PRT
<213> ORGANISM: Pinus taeda
<220> FEATURE:

-continued

<223> OTHER INFORMATION: Pinus taeda loblolly pine expansin

<400> SEQUENCE: 4

```
Met Arg Ser Met Glu Leu Val Lys Ser Ile Ala Leu Ala Ser Leu Leu
1               5                   10                  15

Thr Phe Ile Trp Leu Leu Thr Gly Ala His Gly Tyr Gly Gly Trp Glu
            20                  25                  30

Ser Ala His Ala Thr Phe Tyr Gly Gly Ser Asp Ala Ser Gly Thr Met
        35                  40                  45

Gly Gly Ala Cys Gly Tyr Gly Asn Leu Tyr Ser Gln Gly Tyr Gly Thr
50                  55                  60

Asn Thr Ala Ala Leu Ser Thr Ala Leu Phe Asn Asp Gly Leu Ser Cys
65                  70                  75                  80

Gly Ala Cys Tyr Glu Met Arg Cys Asn Asp Pro Gln Trp Cys Leu
                85                  90                  95

Pro Gly Thr Val Thr Val Thr Ala Thr Asn Phe Cys Pro Pro Asn Asn
            100                 105                 110

Ala Leu Pro Asn Asp Asn Gly Gly Trp Cys Asn Pro Pro Leu Gln His
            115                 120                 125

Phe Asp Met Ala Glu Pro Ala Phe Leu Lys Ile Ala Lys Tyr Arg Gly
130                 135                 140

Gly Ile Val Pro Ile Leu Tyr Thr Arg Val Pro Cys Leu Arg Lys Gly
145                 150                 155                 160

Gly Ile Arg Phe Thr Val Asn Gly His Ser Tyr Phe Asn Leu Val Leu
            165                 170                 175

Ile Thr Asn Val Gly Ala Gly Asp Val His Ala Val Ser Ile Lys
            180                 185                 190

Gly Ser Arg Ser Gly Trp Gln Pro Met Ser Arg Asn Trp Gly Gln Asn
        195                 200                 205

Trp Gln Ser Asn Ser Tyr Leu Asn Gly Gln Ser Leu Ser Phe Gln Val
210                 215                 220

Thr Thr Ser Asp Gly Arg Thr Val Val Ser Asn Val Ala Pro Ser
225                 230                 235                 240

Asn Trp Gln Phe Gly Gln Thr Phe Glu Gly Ser Gln Val
            245                 250
```

<210> SEQ ID NO 5
<211> LENGTH: 234
<212> TYPE: PRT
<213> ORGANISM: Artificial Sequence
<220> FEATURE:
<223> OTHER INFORMATION: alpha expansin consensus sequence, expansin-
    like protein
<220> FEATURE:
<221> NAME/KEY: VARIANT
<222> LOCATION: (1)...(234)
<223> OTHER INFORMATION: Xaa = any amino acid

<400> SEQUENCE: 5

```
Gly Xaa Trp Xaa Xaa Ala Xaa Ala Thr Phe Tyr Gly Gly Xaa Asp Ala
1               5                   10                  15

Ser Gly Thr Xaa Xaa Met Gly Gly Ala Cys Gly Tyr Gly Asn Xaa Tyr
            20                  25                  30

Ser Xaa Gly Tyr Gly Thr Asn Thr Ala Ala Leu Ser Thr Ala Leu Phe
        35                  40                  45

Asn Xaa Gly Xaa Xaa Cys Gly Xaa Cys Tyr Glu Xaa Arg Cys Xaa Xaa
50                  55                  60

Xaa Xaa Xaa Xaa Xaa Cys Leu Pro Gly Xaa Xaa Xaa Val Thr Ala Thr
```

```
                65                  70                  75                  80
Asn Phe Cys Pro Pro Asn Xaa Xaa Leu Pro Xaa Xaa Xaa Gly Gly Trp
                        85                  90                  95

Cys Asn Pro Pro Xaa Xaa His Phe Asp Xaa Xaa Pro Xaa Phe Xaa
                100                 105                 110

Xaa Ile Ala Xaa Tyr Xaa Xaa Gly Xaa Val Pro Xaa Xaa Xaa Arg
            115                 120                 125

Val Pro Cys Xaa Xaa Gly Gly Xaa Xaa Ile Arg Phe Thr Xaa Asn
        130                 135                 140

Gly Xaa Xaa His Ser Tyr Phe Asn Leu Val Leu Xaa Thr Asn Val Xaa
145                 150                 155                 160

Gly Ala Gly Asp Val Xaa Xaa Val Ser Xaa Lys Gly Ser Xaa Xaa Xaa
                165                 170                 175

Gly Trp Gln Xaa Met Ser Arg Asn Trp Gly Gln Asn Trp Gln Ser Asn
            180                 185                 190

Xaa Xaa Leu Xaa Gly Gln Xaa Ser Leu Ser Phe Xaa Val Thr Xaa Ser
        195                 200                 205

Asp Gly Arg Thr Val Xaa Ser Xaa Xaa Xaa Ala Xaa Xaa Xaa Trp Xaa
        210                 215                 220

Phe Gly Gln Thr Xaa Xaa Gly Xaa Xaa Gln
225                 230

<210> SEQ ID NO 6
<211> LENGTH: 265
<212> TYPE: PRT
<213> ORGANISM: Triticum aestivum
<220> FEATURE:
<223> OTHER INFORMATION: Triticum aestivum cultivar Ferdinand bread
      wheat beta-expansin 1 (EXPB1, TaEXPB1)

<400> SEQUENCE: 6

Met Gly Ser Val Ser Tyr Val Leu Ala Ala Ala Val Leu Ala Ala Leu
 1               5                  10                  15

Val Ser Gly Gly Ala Cys Ile Pro Lys Val Pro Pro Gly Pro Asn Ile
                20                  25                  30

Thr Thr Asn Tyr Asn Asn Gln Trp Leu Ser Ala Lys Ala Thr Trp Tyr
            35                  40                  45

Gly Arg Pro Thr Gly Ser Gly Pro Lys Asp Asn Gly Gly Ala Cys Gly
        50                  55                  60

Ile Lys Asp Val Asn Leu Ala Pro Tyr Asn Gly Met Ile Ala Cys Gly
65                  70                  75                  80

Asn Val Pro Ile Phe Lys Asp Gly Lys Gly Cys Gly Ser Cys Tyr Glu
                85                  90                  95

Ile Lys Cys Gln Lys Pro Ser Pro Cys Ser Asp Lys Pro Ile Thr Ile
            100                 105                 110

Phe Ile Thr Asp Lys Asn Tyr Glu Pro Ile Ala Pro Tyr His Ile Asp
        115                 120                 125

Leu Ser Gly Thr Ala Phe Gly Ala Met Ala Thr Pro Gly Lys Glu Gln
        130                 135                 140

Thr Leu Arg Ser Phe Gly Glu Leu Glu Leu Gln Phe Arg Arg Val Arg
145                 150                 155                 160

Cys Lys Tyr Ala Pro Gly Thr Lys Ile Thr Phe His Val Glu Lys Gly
                165                 170                 175

Ser Asn Pro Asn Tyr Leu Ala Val Leu Val Lys Phe Val Ser Asp Asp
            180                 185                 190

Gly Asp Val Val Gln Met Asp Ile Gln Glu Ser Lys Ser Pro Ala Trp
```

```
                    195                 200                 205

Ile Pro Leu Thr Leu Ser Trp Gly Ala Ile Trp Arg Trp Asp Gly Ala
210                 215                 220

Lys Pro Leu Lys Gly Pro Phe Ser Ile Arg Val Thr Ser Glu Ser Gly
225                 230                 235                 240

Lys Lys Leu Ile Ala Lys Asp Val Ile Pro Ala Asn Trp Lys Ala Asp
                    245                 250                 255

Thr Val Tyr Thr Ser Asn Val Gln Phe
            260                 265

<210> SEQ ID NO 7
<211> LENGTH: 264
<212> TYPE: PRT
<213> ORGANISM: Brachypodium sylvaticum
<220> FEATURE:
<223> OTHER INFORMATION: Brachypodium sylvaticum false brome grass
      expansin

<400> SEQUENCE: 7

Met Ala Ser Ser Lys Met Met Leu Ala Met Ala Val Leu Ala Leu
1               5                   10                  15

Leu Ser Leu Ala His Gly Ile Pro Lys Val Pro Gly Pro Asn Ile
                20                  25                  30

Thr Ala Thr Tyr Asn Gly Lys Trp Leu Asp Ala Lys Ser Thr Trp Tyr
                35                  40                  45

Gly Arg Pro Glu Gly Ala Gly Pro Lys Asp Asn Gly Gly Ala Cys Gly
            50                  55                  60

Tyr Lys Asp Val Asp Lys Pro Pro Phe Asn Gly Met Thr Ser Cys Gly
65                  70                  75                  80

Asn Thr Pro Ile Phe Arg Asp Gly Arg Gly Cys Gly Ser Cys Phe Glu
                85                  90                  95

Val Lys Cys Glu Lys Pro Ala Glu Phe Cys Ser Gly Gln Pro Val Leu
                100                 105                 110

Val His Ile Thr Asp Asp Asn Glu Glu Pro Ile Ala Ala Tyr His Phe
                115                 120                 125

Asp Leu Ser Gly Lys Ala Phe Gly Ser Met Ala Lys Lys Gly Gln Glu
        130                 135                 140

Gln Lys Leu Arg Gly Cys Gly Glu Val Glu Ile Gln Phe Arg Arg Val
145                 150                 155                 160

Lys Cys Tyr Tyr Pro Leu Gly Thr Lys Val Thr Tyr His Val Glu Lys
                165                 170                 175

Gly Ser Asn Pro Asn Tyr Leu Ala Leu Leu Val Lys Phe Val Gly Gly
                180                 185                 190

Asp Gly Asp Val Val Ala Val Glu Val Gln Lys Gly Lys Tyr Asn
            195                 200                 205

Trp Ile Pro Leu Lys Glu Ser Trp Gly Ala Val Trp Arg Ile Asp Thr
210                 215                 220

Ala Lys Pro Leu Lys Gly Pro Leu Ser Val Arg Tyr Thr Thr Asp Gly
225                 230                 235                 240

Gly Thr Lys Ala Val Ser Pro Asp Val Ile Pro Glu Lys Trp Lys Pro
                245                 250                 255

Asp Thr Met Tyr Val Ala Lys Tyr
            260

<210> SEQ ID NO 8
<211> LENGTH: 269
<212> TYPE: PRT
```

<213> ORGANISM: Oryza sativa
<220> FEATURE:
<223> OTHER INFORMATION: Oryza sativa Japonica Group cultivar Nipponbare rice beta-expansin (EXPB9)

<400> SEQUENCE: 8

```
Met Gly Ser Leu Thr Thr Asn Ile Val Leu Ala Val Ala Val Val Ala
 1               5                  10                  15

Ala Leu Val Gly Gly Gly Ser Cys Gly Pro Pro Lys Val Pro Pro Gly
            20                  25                  30

Pro Asn Ile Thr Thr Asn Tyr Asn Ala Pro Trp Leu Pro Ala Arg Ala
        35                  40                  45

Thr Trp Tyr Gly Gln Pro Tyr Gly Ser Gly Ser Thr Asp Asn Gly Gly
    50                  55                  60

Ala Cys Gly Ile Lys Asn Val Asn Leu Pro Pro Tyr Asn Gly Met Ile
65                  70                  75                  80

Ser Cys Gly Asn Val Pro Ile Phe Lys Asp Gly Arg Gly Cys Gly Ser
                85                  90                  95

Cys Tyr Glu Val Lys Cys Glu Gln Pro Ala Ala Cys Ser Lys Gln Pro
            100                 105                 110

Val Thr Val Phe Ile Thr Asp Met Asn Tyr Glu Pro Ile Ser Ala Tyr
        115                 120                 125

His Phe Asp Phe Ser Gly Lys Ala Phe Gly Ala Met Ala Cys Pro Gly
    130                 135                 140

Lys Glu Thr Glu Leu Arg Lys Ala Gly Ile Ile Asp Met Gln Phe Arg
145                 150                 155                 160

Arg Val Arg Cys Lys Tyr Pro Gly Gly Gln Lys Val Thr Phe His Val
                165                 170                 175

Glu Lys Gly Ser Asn Pro Asn Tyr Leu Ala Val Leu Val Lys Phe Val
            180                 185                 190

Ala Asp Asp Gly Asp Val Ile Gln Met Asp Leu Gln Glu Ala Gly Leu
        195                 200                 205

Pro Ala Trp Arg Pro Met Lys Leu Ser Trp Gly Ala Ile Trp Arg Met
    210                 215                 220

Asp Thr Ala Thr Pro Leu Lys Ala Pro Phe Ser Ile Arg Val Thr Thr
225                 230                 235                 240

Glu Ser Gly Lys Ser Leu Ile Ala Lys Asp Val Ile Pro Val Asn Trp
                245                 250                 255

Met Pro Asp Ala Ile Tyr Val Ser Asn Val Gln Phe Tyr
            260                 265
```

<210> SEQ ID NO 9
<211> LENGTH: 269
<212> TYPE: PRT
<213> ORGANISM: Zea mays
<220> FEATURE:
<223> OTHER INFORMATION: Zea mays maize beta-expansin 9 (EXPB9), wall loosening protein

<400> SEQUENCE: 9

```
Met Gly Ser Leu Ala Asn Asn Ile Met Val Val Gly Ala Val Leu Ala
 1               5                  10                  15

Ala Leu Val Val Gly Gly Ser Cys Gly Pro Pro Lys Val Pro Pro Gly
            20                  25                  30

Pro Asn Ile Thr Thr Asn Tyr Asn Gly Lys Trp Leu Thr Ala Arg Ala
        35                  40                  45

Thr Trp Tyr Gly Gln Pro Asn Gly Ala Gly Ala Pro Asp Asn Gly Gly
    50                  55                  60
```

```
Ala Cys Gly Ile Lys Asn Val Asn Leu Pro Pro Tyr Ser Gly Met Thr
 65                  70                  75                  80

Ala Cys Gly Asn Val Pro Ile Phe Lys Asp Gly Lys Gly Cys Gly Ser
                 85                  90                  95

Cys Tyr Glu Val Arg Cys Lys Glu Lys Pro Glu Cys Ser Gly Asn Pro
            100                 105                 110

Val Thr Val Phe Ile Thr Asp Met Asn Tyr Glu Pro Ile Ala Pro Tyr
        115                 120                 125

His Phe Asp Leu Ser Gly Lys Ala Phe Gly Ser Leu Ala Lys Pro Gly
    130                 135                 140

Leu Asn Asp Lys Leu Arg His Cys Gly Ile Met Asp Val Glu Phe Arg
145                 150                 155                 160

Arg Val Arg Cys Lys Tyr Pro Ala Gly Gln Lys Ile Val Phe His Ile
                165                 170                 175

Glu Lys Gly Cys Asn Pro Asn Tyr Val Ala Val Leu Val Lys Phe Val
            180                 185                 190

Ala Asp Asp Gly Asp Ile Val Leu Met Glu Ile Gln Asp Lys Leu Ser
        195                 200                 205

Ala Glu Trp Lys Pro Met Lys Leu Ser Trp Gly Ala Ile Trp Arg Met
    210                 215                 220

Asp Thr Ala Lys Ala Leu Lys Gly Pro Phe Ser Ile Arg Leu Thr Ser
225                 230                 235                 240

Glu Ser Gly Lys Lys Val Ile Ala Lys Asp Ile Ile Pro Ala Asn Trp
                245                 250                 255

Arg Pro Asp Ala Val Tyr Thr Ser Asn Val Gln Phe Tyr
            260                 265

<210> SEQ ID NO 10
<211> LENGTH: 75
<212> TYPE: PRT
<213> ORGANISM: Artificial Sequence
<220> FEATURE:
<223> OTHER INFORMATION: beta expansin amino portion consensus sequence,
      expansin-like protein
<220> FEATURE:
<221> NAME/KEY: VARIANT
<222> LOCATION: (1)...(75)
<223> OTHER INFORMATION: Xaa = any amino acid

<400> SEQUENCE: 10

Lys Val Pro Pro Gly Pro Asn Ile Thr Xaa Xaa Tyr Asn Xaa Xaa Trp
 1               5                  10                  15

Leu Xaa Ala Xaa Xaa Thr Trp Tyr Gly Xaa Pro Xaa Gly Xaa Gly Xaa
                 20                  25                  30

Xaa Asp Asn Gly Gly Ala Cys Gly Xaa Lys Xaa Val Xaa Xaa Xaa Pro
            35                  40                  45

Xaa Xaa Gly Met Xaa Xaa Cys Gly Asn Xaa Pro Ile Phe Xaa Asp Gly
        50                  55                  60

Xaa Gly Cys Gly Ser Cys Xaa Glu Xaa Xaa Cys
 65                  70                  75

<210> SEQ ID NO 11
<211> LENGTH: 155
<212> TYPE: PRT
<213> ORGANISM: Artificial Sequence
<220> FEATURE:
<223> OTHER INFORMATION: beta expansin carboxyl portion consensus
      sequence, expansin-like protein
<220> FEATURE:
<221> NAME/KEY: VARIANT
```

<222> LOCATION: (1)...(155)
<223> OTHER INFORMATION: Xaa = any amino acid

<400> SEQUENCE: 11

```
Cys Ser Xaa Xaa Pro Xaa Xaa Xaa Ile Thr Asp Xaa Asn Xaa Glu
 1               5                  10                  15

Pro Ile Xaa Xaa Tyr His Xaa Asp Xaa Ser Gly Xaa Ala Phe Gly Xaa
            20                  25                  30

Xaa Ala Xaa Xaa Gly Xaa Xaa Xaa Leu Arg Xaa Xaa Gly Xaa Xaa
        35                  40                  45

Xaa Xaa Xaa Phe Arg Arg Val Xaa Cys Xaa Tyr Xaa Xaa Gly Xaa Lys
50                      55                  60

Xaa Xaa Xaa His Xaa Glu Lys Gly Xaa Asn Pro Asn Tyr Xaa Ala Xaa
65                  70                  75                  80

Leu Val Lys Phe Val Xaa Xaa Asp Gly Asp Xaa Xaa Xaa Xaa Xaa Xaa
                85                  90                  95

Gln Xaa Xaa Xaa Xaa Xaa Trp Xaa Pro Xaa Xaa Ser Trp Gly
            100                 105                 110

Ala Xaa Trp Arg Xaa Asp Xaa Ala Xaa Xaa Leu Lys Xaa Pro Xaa Ser
        115                 120                 125

Xaa Arg Xaa Thr Xaa Xaa Xaa Gly Xaa Xaa Xaa Xaa Xaa Xaa Asp Xaa
    130                 135                 140

Ile Pro Xaa Xaa Trp Xaa Xaa Asp Xaa Xaa Tyr
145                 150                 155
```

<210> SEQ ID NO 12
<211> LENGTH: 254
<212> TYPE: PRT
<213> ORGANISM: Artificial Sequence
<220> FEATURE:
<223> OTHER INFORMATION: alpha expansin consensus sequence
<220> FEATURE:
<221> NAME/KEY: VARIANT
<222> LOCATION: (1)...(254)
<223> OTHER INFORMATION: Xaa = any amino acid

<400> SEQUENCE: 12

```
Met Xaa Xaa Xaa Xaa Xaa Xaa Xaa Xaa Xaa Leu Xaa Xaa Xaa Xaa
 1               5                  10                  15

Xaa Xaa Xaa Xaa Xaa Xaa Xaa Xaa Xaa Xaa Gly Xaa Trp Xaa
            20                  25                  30

Xaa Ala Xaa Ala Thr Phe Tyr Gly Gly Xaa Asp Ala Ser Gly Thr Met
        35                  40                  45

Gly Gly Ala Cys Gly Tyr Gly Asn Xaa Tyr Ser Xaa Gly Tyr Gly Thr
50                      55                  60

Asn Thr Ala Ala Leu Ser Thr Ala Leu Phe Asn Xaa Gly Xaa Xaa Cys
65                  70                  75                  80

Gly Xaa Cys Tyr Glu Xaa Arg Cys Xaa Xaa Xaa Xaa Xaa Xaa Cys Leu
                85                  90                  95

Pro Gly Xaa Xaa Xaa Val Thr Ala Thr Asn Phe Cys Pro Pro Asn Xaa
            100                 105                 110

Xaa Leu Pro Xaa Xaa Xaa Gly Gly Trp Cys Asn Pro Pro Xaa Xaa His
        115                 120                 125

Phe Asp Xaa Xaa Xaa Pro Xaa Phe Xaa Xaa Ile Ala Xaa Tyr Xaa Xaa
    130                 135                 140

Gly Xaa Val Pro Xaa Xaa Xaa Xaa Arg Val Pro Cys Xaa Xaa Xaa Gly
145                 150                 155                 160

Gly Ile Arg Phe Thr Xaa Asn Gly His Ser Tyr Phe Asn Leu Val Leu
```

```
                165                 170                 175
Xaa Thr Asn Val Xaa Gly Ala Gly Asp Val Xaa Xaa Val Ser Xaa Lys
        180                 185                 190

Gly Ser Xaa Xaa Gly Trp Gln Xaa Met Ser Arg Asn Trp Gly Gln Asn
            195                 200                 205

Trp Gln Ser Asn Xaa Xaa Leu Xaa Gly Gln Ser Leu Ser Phe Xaa Val
        210                 215                 220

Thr Xaa Ser Asp Gly Arg Thr Val Xaa Ser Xaa Xaa Ala Xaa Xaa
225                 230                 235                 240

Xaa Trp Xaa Phe Gly Gln Thr Xaa Xaa Gly Xaa Gln Xaa Xaa
            245                 250

<210> SEQ ID NO 13
<211> LENGTH: 270
<212> TYPE: PRT
<213> ORGANISM: Artificial Sequence
<220> FEATURE:
<223> OTHER INFORMATION: beta expansin consensus sequence
<220> FEATURE:
<221> NAME/KEY: VARIANT
<222> LOCATION: (1)...(270)
<223> OTHER INFORMATION: Xaa = any amino acid

<400> SEQUENCE: 13

Met Xaa Ser Xaa Xaa Xaa Xaa Xaa Xaa Xaa Xaa Ala Val Xaa Ala
1               5                   10                  15

Ala Leu Xaa Xaa Xaa Xaa Xaa Xaa Pro Xaa Lys Val Pro Pro Gly
            20                  25                  30

Pro Asn Ile Thr Xaa Xaa Tyr Asn Xaa Xaa Trp Leu Xaa Ala Xaa Xaa
            35                  40                  45

Thr Trp Tyr Gly Xaa Pro Xaa Gly Xaa Gly Xaa Xaa Asp Asn Gly Gly
        50                  55                  60

Ala Cys Gly Xaa Lys Xaa Val Xaa Xaa Xaa Pro Xaa Xaa Gly Met Xaa
65                  70                  75                  80

Xaa Cys Gly Asn Xaa Pro Ile Phe Xaa Asp Gly Xaa Gly Cys Gly Ser
            85                  90                  95

Cys Xaa Glu Xaa Xaa Cys Xaa Xaa Xaa Xaa Xaa Cys Ser Xaa Xaa
            100                 105                 110

Pro Xaa Xaa Xaa Xaa Ile Thr Asp Xaa Asn Xaa Glu Pro Ile Xaa Xaa
            115                 120                 125

Tyr His Xaa Asp Xaa Ser Gly Xaa Ala Phe Gly Xaa Xaa Ala Xaa Xaa
            130                 135                 140

Gly Xaa Xaa Xaa Xaa Leu Arg Xaa Xaa Gly Xaa Xaa Xaa Xaa Xaa Phe
145                 150                 155                 160

Arg Arg Val Xaa Cys Xaa Tyr Xaa Xaa Gly Xaa Lys Xaa Xaa Xaa His
            165                 170                 175

Xaa Glu Lys Gly Xaa Asn Pro Asn Tyr Xaa Ala Xaa Leu Val Lys Phe
            180                 185                 190

Val Xaa Xaa Asp Gly Asp Xaa Xaa Xaa Xaa Xaa Gln Xaa Xaa Xaa
            195                 200                 205

Xaa Xaa Xaa Trp Xaa Pro Xaa Xaa Xaa Ser Trp Gly Ala Xaa Trp Arg
        210                 215                 220

Xaa Asp Xaa Ala Xaa Xaa Leu Lys Xaa Pro Xaa Ser Xaa Arg Xaa Thr
225                 230                 235                 240

Xaa Xaa Xaa Gly Xaa Xaa Xaa Xaa Xaa Asp Xaa Ile Pro Xaa Xaa
            245                 250                 255

Trp Xaa Xaa Asp Xaa Xaa Tyr Xaa Xaa Xaa Xaa Xaa Xaa Xaa
```

<210> SEQ ID NO 14
<211> LENGTH: 4
<212> TYPE: PRT
<213> ORGANISM: Artificial Sequence
<220> FEATURE:
<223> OTHER INFORMATION: beta expansin subsequence motif (amino acid position ~49-52)

<400> SEQUENCE: 14

Thr Trp Tyr Gly
 1

<210> SEQ ID NO 15
<211> LENGTH: 5
<212> TYPE: PRT
<213> ORGANISM: Artificial Sequence
<220> FEATURE:
<223> OTHER INFORMATION: alpha and beta expansin and swollenin subsequence (alpha expansin amino acid position ~62-67, beta expansin amino acid position ~63-67, swollenin amino acid position ~190-200)

<400> SEQUENCE: 15

Gly Gly Ala Cys Gly
 1               5

<210> SEQ ID NO 16
<211> LENGTH: 42
<212> TYPE: PRT
<213> ORGANISM: Artificial Sequence
<220> FEATURE:
<223> OTHER INFORMATION: alpha expansin consensus subsequence (amino acid position ~48-89)
<220> FEATURE:
<221> NAME/KEY: VARIANT
<222> LOCATION: (1)...(42)
<223> OTHER INFORMATION: Xaa = any amino acid

<400> SEQUENCE: 16

Ala Thr Phe Tyr Gly Gly Xaa Asp Ala Ser Gly Thr Xaa Xaa Met Gly
 1               5                  10                  15

Gly Ala Cys Gly Tyr Gly Asn Xaa Tyr Ser Xaa Gly Tyr Gly Thr Asn
                20                  25                  30

Thr Ala Ala Leu Ser Thr Ala Leu Phe Asn
                35                  40

<210> SEQ ID NO 17
<211> LENGTH: 24
<212> TYPE: PRT
<213> ORGANISM: Artificial Sequence
<220> FEATURE:
<223> OTHER INFORMATION: alpha expansin consensus subsequence (amino acid position ~117-140)
<220> FEATURE:
<221> NAME/KEY: VARIANT
<222> LOCATION: (1)...(24)
<223> OTHER INFORMATION: Xaa = any amino acid

<400> SEQUENCE: 17

Val Thr Ala Thr Asn Phe Cys Pro Pro Asn Xaa Xaa Leu Pro Xaa Xaa
 1               5                  10                  15

Xaa Gly Gly Trp Cys Asn Pro Pro
                20

<210> SEQ ID NO 18
<211> LENGTH: 35

```
<212> TYPE: PRT
<213> ORGANISM: Artificial Sequence
<220> FEATURE:
<223> OTHER INFORMATION: alpha expansin consensus subsequence (amino
      acid position ~179-213)
<220> FEATURE:
<221> NAME/KEY: VARIANT
<222> LOCATION: (1)...(35)
<223> OTHER INFORMATION: Xaa = any amino acid

<400> SEQUENCE: 18

Ile Arg Phe Thr Xaa Asn Gly Xaa Xaa His Ser Tyr Phe Asn Leu Val
1               5                   10                  15

Leu Xaa Thr Asn Val Xaa Gly Ala Gly Asp Val Xaa Xaa Val Ser Xaa
            20                  25                  30

Lys Gly Ser
        35

<210> SEQ ID NO 19
<211> LENGTH: 33
<212> TYPE: PRT
<213> ORGANISM: Artificial Sequence
<220> FEATURE:
<223> OTHER INFORMATION: alpha expansin consensus subsequence (amino
      acid position ~221-253)
<220> FEATURE:
<221> NAME/KEY: VARIANT
<222> LOCATION: (1)...(33)
<223> OTHER INFORMATION: Xaa = any amino acid

<400> SEQUENCE: 19

Met Ser Arg Asn Trp Gly Gln Asn Trp Gln Ser Asn Xaa Xaa Leu Xaa
1               5                   10                  15

Gly Gln Xaa Ser Leu Ser Phe Xaa Val Thr Xaa Ser Asp Gly Arg Thr
            20                  25                  30

Val

<210> SEQ ID NO 20
<211> LENGTH: 13
<212> TYPE: PRT
<213> ORGANISM: Artificial Sequence
<220> FEATURE:
<223> OTHER INFORMATION: beta expansin consensus subsequence (amino
      acid position ~28-40)
<220> FEATURE:
<221> NAME/KEY: VARIANT
<222> LOCATION: (1)...(13)
<223> OTHER INFORMATION: Xaa = any amino acid

<400> SEQUENCE: 20

Lys Val Pro Pro Gly Pro Asn Ile Thr Xaa Xaa Tyr Asn
1               5                   10

<210> SEQ ID NO 21
<211> LENGTH: 18
<212> TYPE: PRT
<213> ORGANISM: Artificial Sequence
<220> FEATURE:
<223> OTHER INFORMATION: beta expansin consensus subsequence (amino
      acid
      position ~82-99)
<220> FEATURE:
<221> NAME/KEY: VARIANT
<222> LOCATION: (1)...(18)
<223> OTHER INFORMATION: Xaa = any amino acid

<400> SEQUENCE: 21

Cys Gly Asn Xaa Pro Ile Phe Xaa Asp Gly Xaa Gly Cys Gly Ser Cys
1               5                   10                  15
```

```
Xaa Glu

<210> SEQ ID NO 22
<211> LENGTH: 22
<212> TYPE: PRT
<213> ORGANISM: Artificial Sequence
<220> FEATURE:
<223> OTHER INFORMATION: beta expansin consensus subsequence (amino
      acid position ~118-139)
<220> FEATURE:
<221> NAME/KEY: VARIANT
<222> LOCATION: (1)...(22)
<223> OTHER INFORMATION: Xaa = any amino acid

<400> SEQUENCE: 22

Ile Thr Asp Xaa Asn Xaa Glu Pro Ile Xaa Xaa Tyr His Xaa Asp Xaa
1               5                   10                  15

Ser Gly Xaa Ala Phe Gly
            20

<210> SEQ ID NO 23
<211> LENGTH: 21
<212> TYPE: PRT
<213> ORGANISM: Artificial Sequence
<220> FEATURE:
<223> OTHER INFORMATION: beta expansin consensus subsequence (amino
      acid position ~178-198)
<220> FEATURE:
<221> NAME/KEY: VARIANT
<222> LOCATION: (1)...(21)
<223> OTHER INFORMATION: Xaa = any amino acid

<400> SEQUENCE: 23

Glu Lys Gly Xaa Asn Pro Asn Tyr Xaa Ala Xaa Leu Val Lys Phe Val
1               5                   10                  15

Xaa Xaa Asp Gly Asp
            20
```